(12) United States Patent
Yen et al.

(10) Patent No.: US 9,023,834 B2
(45) Date of Patent: *May 5, 2015

(54) LYOPHILIZATION FORMULATION

(75) Inventors: Chi-Feng Yen, Taipei (TW); Judy Yuan, Annandale, VA (US); Chi-Hsin Richard King, Holladay, UT (US)

(73) Assignee: TaiGen Biotechnology Co., Ltd., Taipei (TW)

( * ) Notice: Subject to any disclaimer, the term of this patent is extended or adjusted under 35 U.S.C. 154(b) by 637 days.

This patent is subject to a terminal disclaimer.

(21) Appl. No.: 12/617,238

(22) Filed: Nov. 12, 2009

(65) Prior Publication Data

US 2010/0120719 A1 May 13, 2010

Related U.S. Application Data

(60) Provisional application No. 61/114,144, filed on Nov. 13, 2008.

(51) Int. Cl.
| | | |
|---|---|---|
| *A61K 31/675* | (2006.01) | |
| *A61K 31/497* | (2006.01) | |
| *C07F 9/6558* | (2006.01) | |
| *A61K 31/496* | (2006.01) | |
| *A61K 31/527* | (2006.01) | |
| *C07D 239/70* | (2006.01) | |
| *C07D 403/04* | (2006.01) | |
| *C07F 9/6571* | (2006.01) | |
| *C07F 9/6584* | (2006.01) | |

(52) U.S. Cl.
CPC ............ *C07F 9/65583* (2013.01); *A61K 31/496* (2013.01); *A61K 31/527* (2013.01); *A61K 31/675* (2013.01); *C07D 239/70* (2013.01); *C07D 403/04* (2013.01); *C07F 9/65781* (2013.01); *C07F 9/65846* (2013.01)

(58) Field of Classification Search
None
See application file for complete search history.

(56) References Cited

U.S. PATENT DOCUMENTS

| | | | |
|---|---|---|---|
| 5,034,560 | A | 7/1991 | Cesa et al. |
| 5,665,760 | A | 9/1997 | Brown et al. |
| 6,306,902 | B1 | 10/2001 | Anderson et al. |
| 6,420,354 | B1 | 7/2002 | Marquess et al. |
| 7,501,412 | B2 | 3/2009 | Fujio et al. |
| 2003/0109514 | A1 | 6/2003 | Lauria et al. |
| 2005/0124640 | A1 | 6/2005 | Cardozo et al. |
| 2006/0013836 | A1 | 1/2006 | Bandyopadhyay et al. |
| 2006/0281712 | A1* | 12/2006 | Yen et al. .................. 514/85 |
| 2006/0293324 | A1 | 12/2006 | Yen et al. |
| 2009/0143302 | A1* | 6/2009 | Yen et al. .................. 514/12 |
| 2009/0264339 | A1* | 10/2009 | Yen et al. .................. 514/8 |

FOREIGN PATENT DOCUMENTS

| | | |
|---|---|---|
| EP | 834507 | 8/1998 |
| WO | WO 93/01498 | 1/1993 |
| WO | WO 95/13312 | 5/1995 |
| WO | WO 95/23609 | 9/1995 |
| WO | WO 97/20823 | 6/1997 |
| WO | WO 97/46250 | 12/1997 |
| WO | WO 98/24782 | 6/1998 |
| WO | WO 99/50249 | 10/1999 |
| WO | WO 00/20358 | 4/2000 |
| WO | WO 01/47897 | 7/2001 |
| WO | WO 02/50065 | 6/2002 |
| WO | WO 02/057259 | 7/2002 |
| WO | WO 03/024448 | 3/2003 |
| WO | WO 03/028641 | 4/2003 |
| WO | WO 2004/052862 | 6/2004 |
| WO | WO 2004/067516 | 8/2004 |
| WO | WO 2004/069823 | 8/2004 |
| WO | WO2005/028427 | 3/2005 |

OTHER PUBLICATIONS

Kofi Bedu-Addo ('Understanding Lyophilization Formulation Development' in Pharmaceutical Technology, 2004).*
Larsen et al., "Hylan and Hylan Derivatives in Drug Deliver," Cosmetic and Pharmaceutical Applications of Polymers, 147-157, 1991.
Lofas, "Dextarn modified self-assembled monolayer surfaces for use in bioapplication analysis with surface Plasmon resonance," Pure & Appl. Chem. 67:829-834, 1995.
Prestwich, "Biomaterials from Chemically-Modified Hyaluronan," Glycoforum, 2001.
Goendoes et al., "An Efficient Synthesis of cis- and trns-2-Aminocyclohexanecarboxamides and Their N-Substituted Derivates," Liebigs Ann. Chem. 591-593, 1991.
Roberts et al., "Synthesis of Some 4-Substituted Biocyclo[2.2.2]octane-1-carboxylic Acids", JACS, 75:637-640, 1953.
Kanuma et al., "Discovery of 4-(dimethylamino)quinazolines as potent and selective antagonists for the melanin-concentrating hormone receptor 1", Bioorganic & Medicinal Chemistry Letters 15:2565-2569, 2005.
Campagna et al., "A Convenient Synthesis of Nitrites from Primary Anodes Under Mild Conditions," Tetrahedron Letters; the International Organ for the Rapid Publication of Preliminary Communications in Organic Chemistry, 1913-1816, 1977.
Klenke et al., "Nitrite Reduction in the Presence of Boc-Protected Amino Groups by Catalytic Hydrogenation over Palladium-Activated Raney-Nickel" J. Org. Chem. 66:2480-2483, 2001.
Kuo et al. "A convenient new procedure for converting primary amides into nitrites" Chem. Commun. 2007, 301-303.
Li et al. "Preparation of Fluorescent Nonpetidic Neuropeptide Y Receptor Eigands: Analogues of the Quinazoline-type Antiobesity Y Antagonist CGP 71683A" Arch. Pharm. Pharm. Med. Chem. 2003, 336, 585-590.
MedicineNet.com, "Definition of Retinopathy", 2003, downloaded from http://www.medterms.com/script/main/art.asp?articlekey=22185 on Aug. 14, 2009, p. 1 of 1.

(Continued)

*Primary Examiner* — Craig Ricci

(74) *Attorney, Agent, or Firm* — Cesari and McKenna, LLP

(57) ABSTRACT

This invention relates to a pharmaceutical kit containing a lyophilized preparation of a pyrimidine compound described in the specification. Also disclosed is a lyophilization process for making this preparation.

26 Claims, No Drawings

(56) References Cited

OTHER PUBLICATIONS

MedicineNet.com, "Definition of Ischemia", 1998, downloaded from http://www.medterms.com/script/main/art.asp?articlekey=4052 on Aug. 14, 2009, p. 1 of 1.

Suggitt et al.,; "50 Years of Preclinical Anticancer Drug Screening: Empirical to Target-Driven Approaches"; Clinical Cancer Research, 2005, vol. 11, pp. 971-981.

Gura, "Systems for Identifying New Drugs are Often Faulty"; Science, 1997, vol. 278, 1041-1042.

* cited by examiner

LYOPHILIZATION FORMULATION

CROSS REFERENCE TO RELATED APPLICATIONS

This application claims priority to U.S. Provisional Application No. 61/114,144, filed Nov. 13, 2008. The content of the prior application is hereby incorporated by reference in its entirety.

BACKGROUND OF THE INVENTION

Some active pharmaceutical ingredients in aqueous solutions are labile and decompose during storage. Suitable formulation is therefore needed to meet the shelf-life requirement.

SUMMARY

This invention is based on an unexpected discovery that pharmaceutically active pyrimidine compounds in certain formulations are less hygroscopic and more stable than the compounds themselves.

In one aspect, this invention relates to a pharmaceutical kit including a sealed container and a lyophilized preparation of a pharmaceutically active compound disposed in the container, the compound having formula (I):

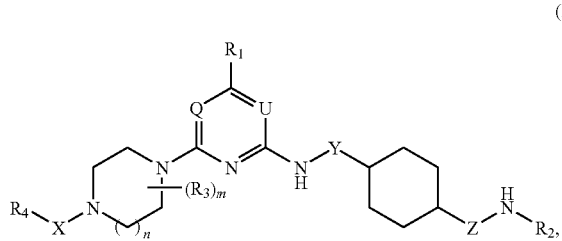

(I)

wherein each Q and U, independently, is CH or N, provided that at least one of Q and U is N; each of X, Y, and Z, independently, is $C_{1-5}$ alkylene or deleted; m is 0, 1, 2, 3, 4, or 5; n is 0, 1 or 2; $R_1$ is H, $C_1$-$C_{10}$ alkyl, $C_3$-$C_{20}$ cycloalkyl, $C_3$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$; $R_2$ is $C_1$-$C_{10}$ alkyl, $C_3$-$C_{20}$ cycloalkyl, $C_3$-$C_{20}$ heterocycloalkyl, aryl, heteroaryl, or $C_1$-$C_{10}$ alkyl, optionally substituted with $C_1$-$C_{10}$ alkyl, $C_3$-$C_{20}$ cycloalkyl, $C_3$-$C_{20}$ heterocycloalkyl, or $N(R_cR_d)$; each of $R_3$ groups, independently, is $C_1$-$C_{10}$ alkyl, $C_3$-$C_{20}$ cycloalkyl, $C_3$-$C_{20}$ heterocycloalkyl, aryl, heteroaryl, halo, CN, $OR_e$, $COOR_e$, $OC(O)R_e$, $C(O)R_e$, $C(O)NR_eR_f$, or $NR_eR_f$; or $(R_3)_m$ is $C_{1-5}$ alkylene bonded to two carbon atoms of the ring to which it is attached or $C_{2-8}$ alkylene bonded to one carbon atom of the ring to which it is attached; and $R_4$ is $P(=O)(OR_g)(OR_i)$, $P(=O)(NHR_g)(OR_i)$, $P(=O)(NR_g)(NR_i)$, $S(=O)_2OR_g$, or $S(=O)_2R_g$; in which each of $R_a$, $R_b$, $R_c$, $R_d$, $R_e$, $R_f$, $R_g$ and independently, is H, $C_1$-$C_{10}$ alkyl, $C_3$-$C_{20}$ cycloalkyl, $C_3$-$C_{20}$ heterocycloalkyl, aryl, heteroaryl, or —C(O)R, R being H, $C_1$-$C_{10}$ alkyl, $C_3$-$C_{20}$ cycloalkyl, $C_3$-$C_{20}$ heterocycloalkyl, aryl, or heteroaryl; or $R_a$ and $R_b$ are linked and together form $C_{2-8}$ alkylene, $R_e$ and $R_d$ are linked and together form $C_{2-8}$ alkylene, $R_e$ and $R_f$ are linked and together form $C_{2-8}$ alkylene, or $R_g$ and $R_i$ are linked and together form $C_{1-5}$ alkylene.

A subset of the compounds described above feature that: U is N; X is —$CH_2$—, —$CH_2CH_2$— or —$CH_2CH_2CH_2$—; Y is —$CH_2$ or deleted; Z is —$CH_2$—; m is 0, 1, or 2; n is 1 or 2; $R_1$ is $NH_2$; $R_2$ is $C_{1-5}$ alkyl substituted $N(R_eR_d)$, e.g., —$CH_2CH_2$—$N(R_eR_d)$, or —$CH_2CH_2CH_2$—$N(R_eR_d)$, in which $R_e$ is H and $R_d$ is $C_1$-$C_{10}$ alkyl, $C_3$-$C_{20}$ cycloalkyl, $C_3$-$C_{20}$ heterocycloalkyl, aryl, or heteroaryl, or $R_e$ and $R_d$ are linked and together form $C_{4-6}$ alkylene; $R_3$ is $C_1$-$C_3$ alkyl, $C_3$-$C_8$ cycloalkyl, $C_3$-$C_8$ heterocycloalkyl, aryl, heteroaryl, halo, CN, $OR_e$, or $C(O)NR_eR_f$; or $R_3$ is $C_{1-2}$ alkylene bonded to two carbon atoms of the ring to which it is attached or $C_{2-5}$ alkylene bonded to one carbon atom of the ring to which it is attached; and $R_4$ is $P(=O)(OH)_2$, $P(=O)(OH)(OCH_2CH_3)$, $P(=O)(OCH_2CH_3)_2$,

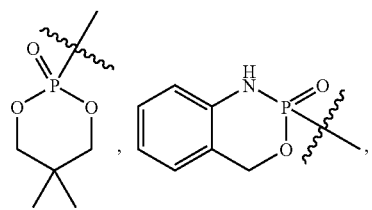

$S(=O)_2OH$, $S(=O)_2CH_3$, or $S(=O)_2Ph$.

The term "alkyl" refers to a saturated or unsaturated, linear or branched hydrocarbon moiety, such as —$CH_3$, —$CH_2$—CH=$CH_2$, or branched —$C_3H_7$. The term "alkylene" refers to a divalent, saturated or unsaturated, linear or branched hydrocarbon moiety, such as —$CH_2$—, —$CH_2CH_2$—, —$CH_2CH_2CH_2$—, or —CH=CH—. The term "cycloalkyl" refers to a saturated or unsaturated, non-aromatic, monocyclic, bicyclic, tricyclic, or tetracyclic hydrocarbon moiety, such as cyclohexyl, cyclohexen-3-yl, or adamantyl. The term "heterocycloalkyl" refers to a saturated or unsaturated, non-aromatic, monocyclic, bicyclic, tricyclic, or tetracyclic moiety having one or more ring heteroatoms (e.g., N, O, or S), such as 4-tetrahydropyranyl or 4-pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkylene, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl and alkylene include all of the above-recited substituents except $C_1$-$C_{10}$ alkyl, $C_2$-$C_{10}$ alkenyl, and $C_2$-$C_{10}$ alkynyl. Cycloalkyl, heterocycloalkyl, aryl, and heteroaryl can also be fused with each other.

The compounds described above include the compounds themselves, as well as their salts, prodrugs, and solvates, if applicable. A salt, for example, can be formed between an anion and a positively charged group (e.g., amino) on a compound having one of the above formulas. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a compound having one of the above formulas. Suitable cations include sodium ion, potassium ion, magnesium ion, calcium ion, and an ammonium cation such as tetramethylammonium ion. The compounds also include those salts containing quaternary nitrogen atoms. For calculation simplicity, unless otherwise stated, the weight of a compound mentioned herein refers to that of the free base form of that compound. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Shown below are exemplary pyrimidine compounds that can be used to practice this invention:

Compound 1

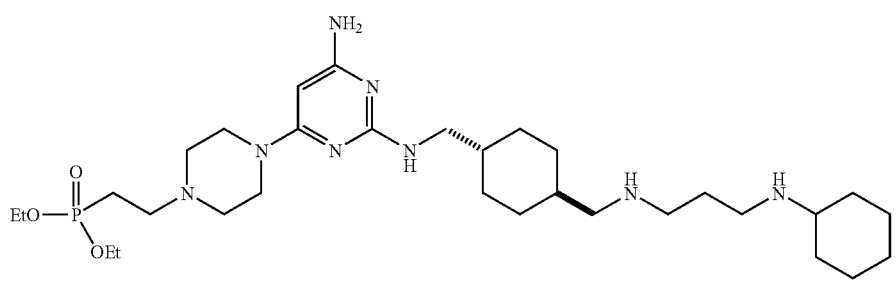

Compound 2

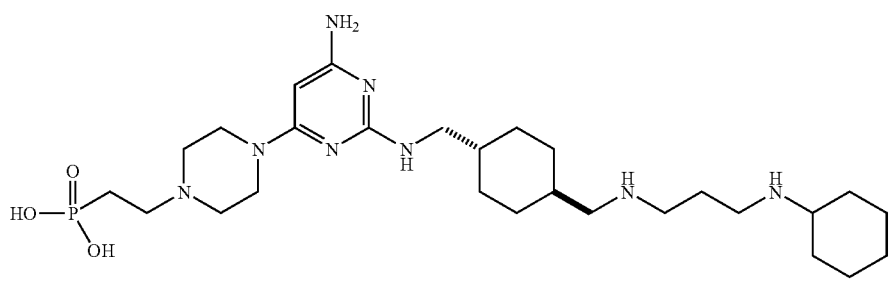

Compound 3

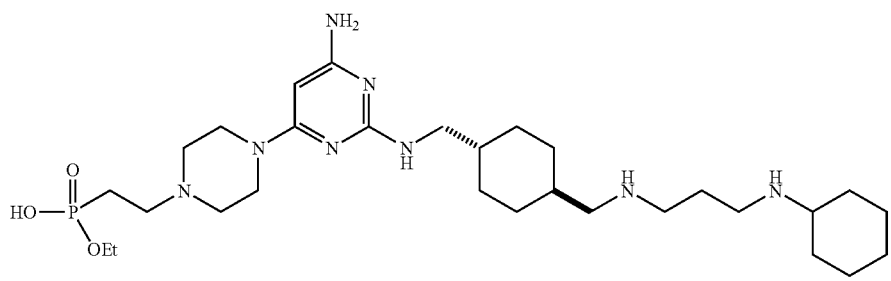

Compound 4

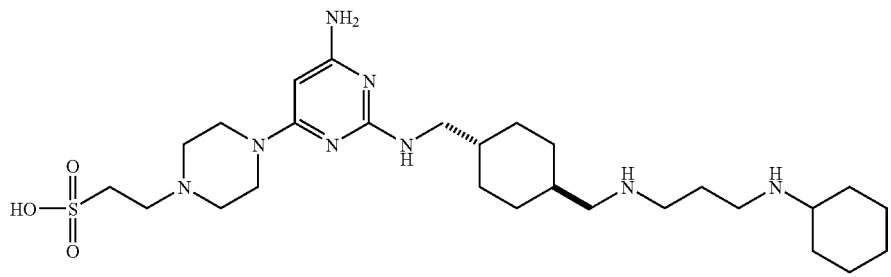

Compound 5
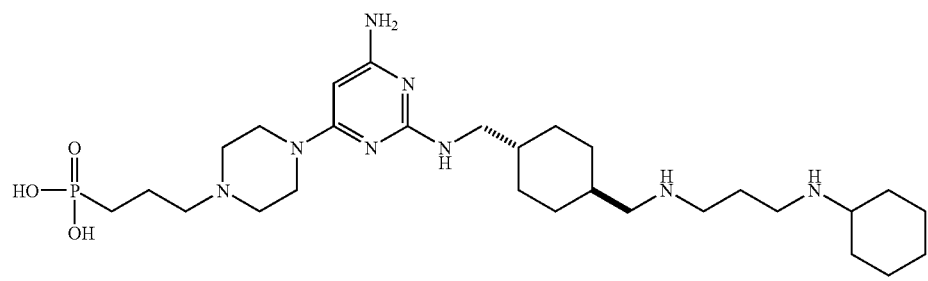
Compound 6
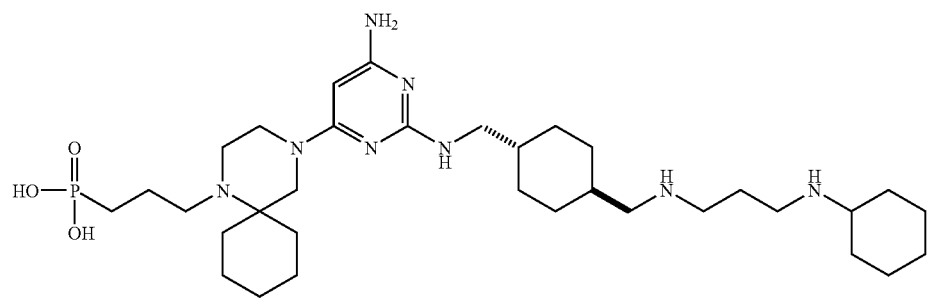
Compound 7
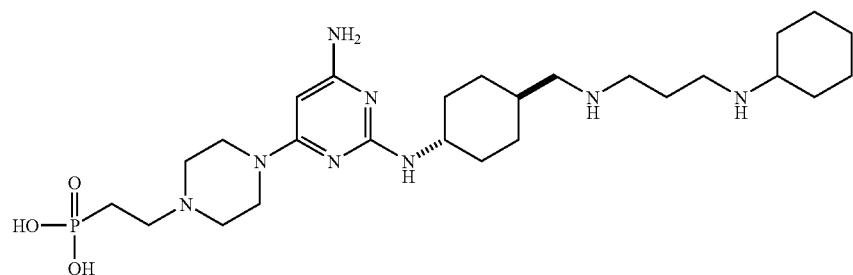
Compound 8
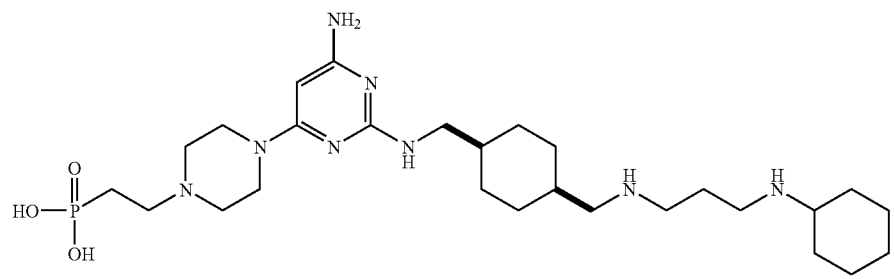
Compound 9
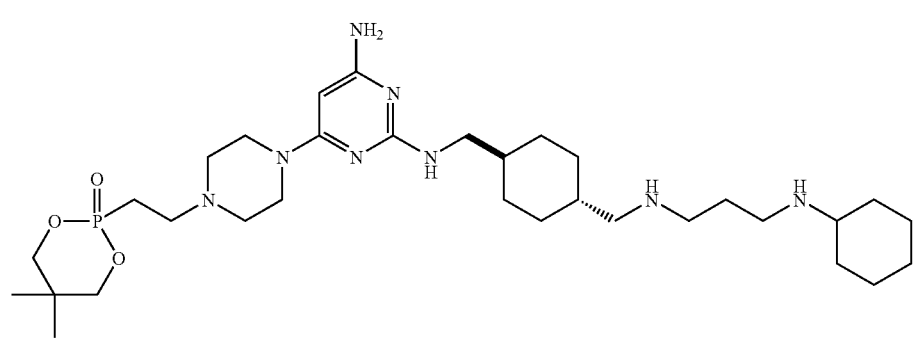

-continued

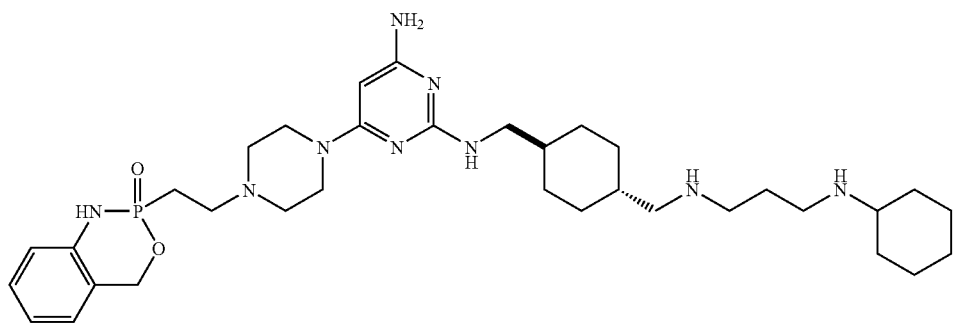

Compound 10

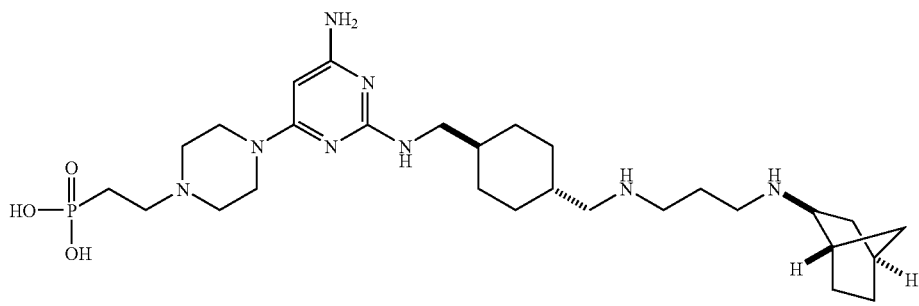

Compound 11

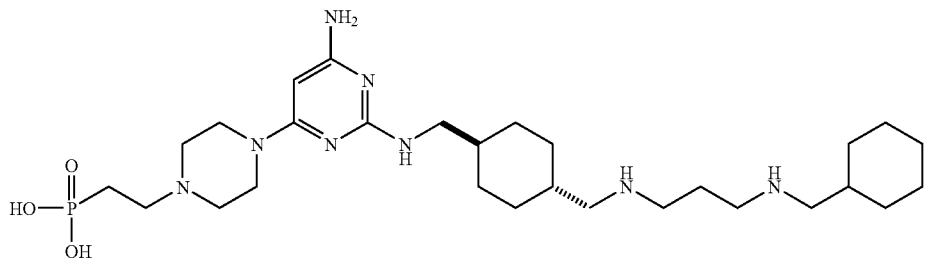

Compound 12

The lyophilized preparation in the above-described pharmaceutical kit may also contain a bulking agent, a tonicity adjuster, or both. As an example, the preparation contains mannitol or dextran as the bulking agent and sodium chloride as the tonicity adjuster. The weight ratio of the compound, the bulking agent, and the tonicity adjuster can be 1 to 25:10 to 50:0.01 to 6 or 1 to 50:0.01 to 50:0.01 to 0.9.

In another aspect, this invention relates to a process of making the above-described lyophilized preparation. The process includes providing an aqueous solution containing a compound of formula (I); cooling the solution to a temperature between −80° C. and −10° C.; and vacuuming the solution between −80° C. and −10° C. for 15-100 hours, and then between −9° C. and 35° C. for 10-200 hours.

Optionally, the aqueous solution also contains a bulking agent, a tonicity adjuster, or both. As an example, the solution contains a compound of formula (I), mannitol or dextran (as a bulking agent), and/or sodium chloride or glycerol (as a tonicity adjuster), the concentrations of the compound, the mannitol/dextran, and the sodium chloride/glycerol being respectively 1-25 mg/ml, 10-50 mg/ml, and 0.01-6 mg/ml, or 1-50 mg/ml, 0.01-50 mg/ml, and 0.01-0.9 mg/ml.

The compounds of formula (I) are effective in inhibiting the binding between SDF-1 and chemokine receptors (e.g., CXCR4 receptor). See U.S. application Ser. No. 12/263,671. Thus, in another aspect, this invention relates to use of the pharmaceutical kit, which contains a lyophilized preparation of one of these pharmaceutically active compounds, in treating a medical condition associated with the CXCR4/SDF-1 pathway, such as an inflammatory or immune disease, a developmental or degenerative disease, a tissue injury, or cancer.

Also within the scope of this invention is use of the above-described lyophilized preparation for the manufacture of a medicament for the just-mentioned treatment.

An inflammatory disease is characterized by a local or systemic, acute or chronic inflammation. Examples include retinopathy (e.g., diabetic retinopathy and proliferative retinopathy), inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease (ILD), idiopathic pulmonary fibrosis, and ILD associated with rheumatoid arthritis), macular edema, asthma, and allergic rhinitis.

An immune disease is characterized by a hyper- or hyporeaction of the immune system. Examples include, but are not limited to, autoimmune diseases (e.g., rheumatoid arthritis, psoriatic arthritis, systemic lupus erythematosus, myasthenia gravis, Type I diabetes mellitus, glomerulonephritis, autoimmune throiditis, ankylosing spondylitis, systemic sclerosis, and multiple sclerosis), acute and chronic inflammatory diseases (e.g., systemic anaphylaxia or hypersensitivity responses, drug allergies, insect sting allergies, graft rejection, including allograft rejection, and graft-versus-host disease), Sjogren's syndrome, and human immunodeficiency virus infection.

Developmental diseases are growth or differentiation related disorders that lead to loss-of-function or gain-of-function. Degenerative diseases generally refer to change of a tissue to a lower or less functional form. Examples of a developmental or degenerative disease include age-related macular degeneration, corneal neovascularization, iris neovascularization, spinal muscular atrophy, Duchenne muscular dystrophy, Parkinson's disease, and Alzheimer's disease. Tissue injuries can be caused by oxidative stress (e.g., ischemia-reperfusion in stroke or myocardial infarction), complement activation, graft rejection, chemicals (e.g., alcohol-induced liver damage or mucosal tissue injuries in cancer therapy), viral infection (e.g., glomerular injuries associated with hepatitis C infection), and mechanical forces (e.g., sports injury). Examples of tissue injuries include brain injury, nerve injury, heart injury, liver damage, skeletal muscle injury, kidney damage, pancreatic injury, lung injury, skin injury, limb ischemia, silent ischemia, cardiac ischemia, and gastrointestinal tract injury.

Cancer is a class of diseases in which a group of cells having the capacity for autonomous growth, i.e., an abnormal state or condition characterized by rapidly proliferating cell growth and sometimes tumor metastasis. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, colon cancer, kidney cancer, thyroid cancel, haematopoietic cancer, and cancer of unknown primary site.

The details of one or more embodiments of the invention are set forth in the description below. Other features, objects, and advantages of the invention will be apparent from the description and from the claims.

DETAILED DESCRIPTION OF THE INVENTION

The compounds of formula (I) used in this invention can be prepared by methods well known in the art. Scheme I below shows a synthetic route for synthesizing certain exemplary compounds. Pyrimidine compound (i) containing two halo groups ($R_3$ and $R_6$ are halo) selectively reacts with an amino compound (ii) to give 2-aminopyrimidine compound (iii), which couples with piperazine compound (iv) to afford 6-piperazyl-2-aminopyrimidine compound (v). Compound (v) is further modified to obtain desired phosphonate compound (vi) or phosphonic acid (vii). The compounds thus synthesized can be purified by a method such as column chromatography, high-pressure liquid chromatography, or recrystallization.

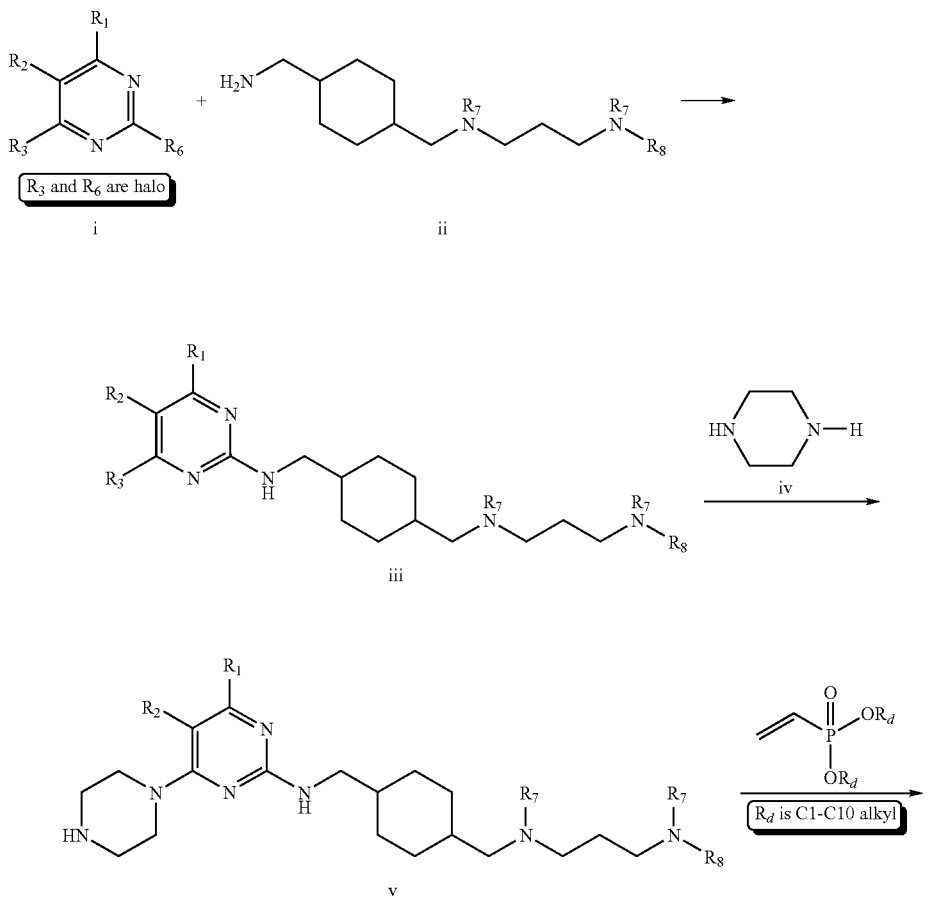

-continued

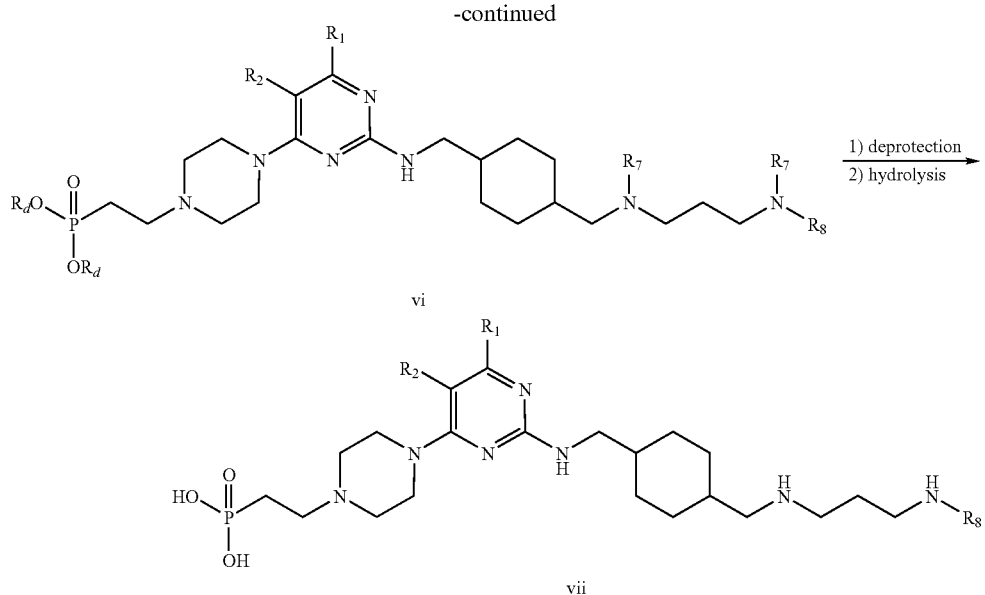

vi vii

The synthetic route outlined in Scheme 1 can be modified in various manners to prepare other compounds of formula (I). For example, an amino compound other than compound (II) can be used, or piperazine compound (iv) can be replaced by an imidazolidine or diazepane compound.

The chemical agents used in the methods described above are either commercially available or can be prepared by methods known in the art. The methods may additionally include steps, either before or after the steps described specifically herein, to add or remove suitable protecting groups in order to ultimately allow synthesis of the compounds. Moreover, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of formula (I) may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

To practice this invention, one can prepare an aqueous solution containing a compound of formula (I) at a predetermined concentration. The solution may also contain a bulking agent. The bulking agent provides the bulk to the final solid product and can produce a crystalline structure with good mechanical properties. Examples of a bulking agent include mannitol, sucrose, glucose, and dextran. The concentrations of the compound and the bulking agent can be respectively 1-25 mg/ml and 10-50 mg/ml, or 1-50 mg/ml and 0.01-50 mg/ml. The bulking agent can also be used to control the osmolality of the solution to obtain a nearly isotonitic solution. If necessary, the solution may also contain a tonicity adjuster to further modify the osmolality of the solution. Examples of a tonicity adjuster include sucrose, glycine, glycerol, sodium chloride, potassium chloride, sodium bromide, and potassium bromide. The preferred osmolality is 250-300 mmol/kg. In one example, an aqueous solution contains 5 mg/ml of the compound, 30 mg/ml of mannitol, and 3 mg/ml of sodium chloride.

The solution may further contain one or more ingredients, such as a buffering agent and a stabilizer. A buffering agent is used to stabilize pH of the solution. Examples of a buffering agent include acetate, citrate, tartarate, lactate, succinate, malate, and phosphate. A stabilizer can be a substance that forms an amorphous sugar glass and thereby stabilizes the compound in the solution. Examples of a stabilizer include sucrose, trehalose, glucose, lactose, and maltose.

All of these ingredients can be added at any stage during preparation of the solution. The suitable concentration of an ingredient for conferring the intended effect can be readily understood or determined by conventional methods.

The solution may be filtered to remove particles and microbe. A clear and sterile solution can therefore be obtained. The filtration membrane pore size ranges from 0.1 to 10 μm, e.g., 0.22 μm.

The pH of the solution may need to be modified to a value at which the compound is most stable. The agent used to adjust the pH can be an organic or inorganic acid or base, such as HCl, acetic acid, sodium hydroxide, or ammonia.

To prepare the pharmaceutical kit, one can transfer the solution to a container, e.g., a vial, in a predetermined volume first and then subject the solution to a lyophilization process. Alternatively, one can lyophilize the solution in a large volume and then place a predetermined amount of the lyophilized preparation in a container.

Lyophilization includes three stages: freezing, primary drying, and secondary drying.

During the freezing stage, the temperature of the solution is lowered to a low temperature (e.g., −40° C. to −50° C.) over 10 min to 5 hours. Pure crystalline ice forms from a portion of the solution. It results in increasing the concentration and viscosity of the remaining solution such that it cannot undergo crystallization. Ultimately, this highly concentrated and viscous solution solidified to yield a combined crystalline-amorphous phase.

During the primary drying stage, the ice in the frozen solution is removed by sublimation. As an example, the sublimation is carried out under 10-655 μbar at a temperature between −20° C. and −50° C. for 15-100 hours. Note that it is preferred that the product be maintained in the solid state so as to retain the structure formed during the freezing stage.

During the secondary drying stage, the temperature is allowed to increase (e.g., between −9° C. and 35° C.) or the pressure is reduced to remove the remaining bound water. This stage may last 10-200 hours to provide a solid preparation with the desired residual moisture.

The lyophilized preparation thus obtained can be stored for later use. It is preferred to fill the container including the lyophilized preparation with an inert gas (e.g., nitrogen) and seal it to further prevent degradation and microbial contamination.

One can use the pharmaceutical kit in treating a medical condition by administration to a subject in need of the treatment an effective amount of the lyophilized preparation contained in the kit.

As used herein, the term "treating" or "treatment" is defined as the administration of an effective amount of the lyophilized preparation to a subject, who has a disease associated with the CXCR4/SDF-1 pathway, a symptom of the disease, or a predisposition toward the disease, with the purpose to cure, alleviate, relieve, remedy, or ameliorate the disease, the symptom of the disease, or the predisposition toward the disease. The term "an effective amount" refers to an amount of the lyophilized preparation required to confer a therapeutic effect on the treated subject.

To treat a disease associated with the CXCR4/SDF-1 pathway, the lyophilized preparation described above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be prepared by mixing the lyophilized preparation in the pharmaceutical kit of this invention with a non-toxic parenterally acceptable diluent or solvent, such as water or 1,3-butanediol, to form a solution or suspension. In addition, fixed oils can be employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

The lyophilized preparation contained in the pharmaceutical kit can also be orally administered to a subject. In addition, the lyophilized preparation can be further processed to form any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added to the composition of this invention. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

An eye drop or ointment composition can also be prepared and used according to methods well known in the art.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Chemical Synthesis (1) Preparation of Compound 1

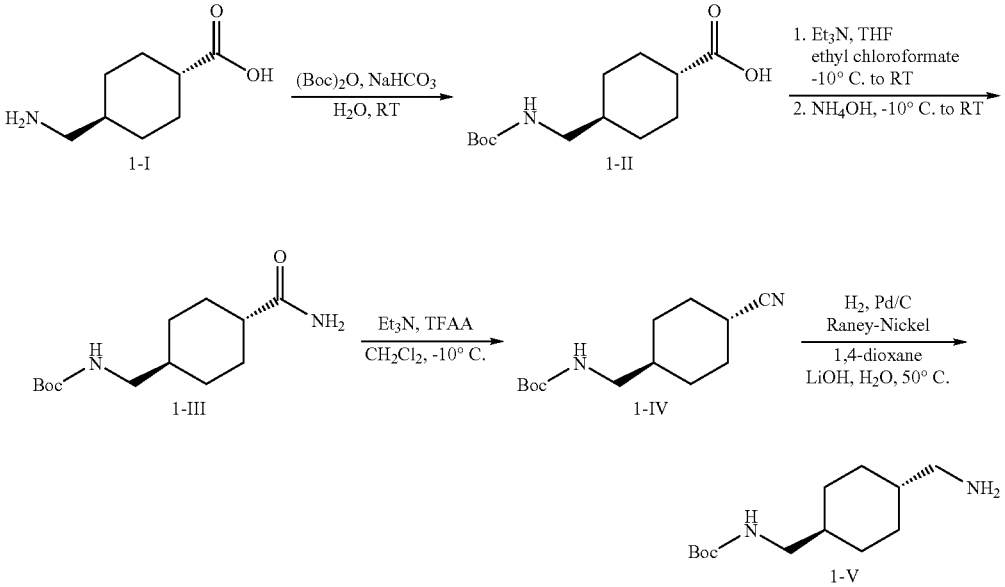

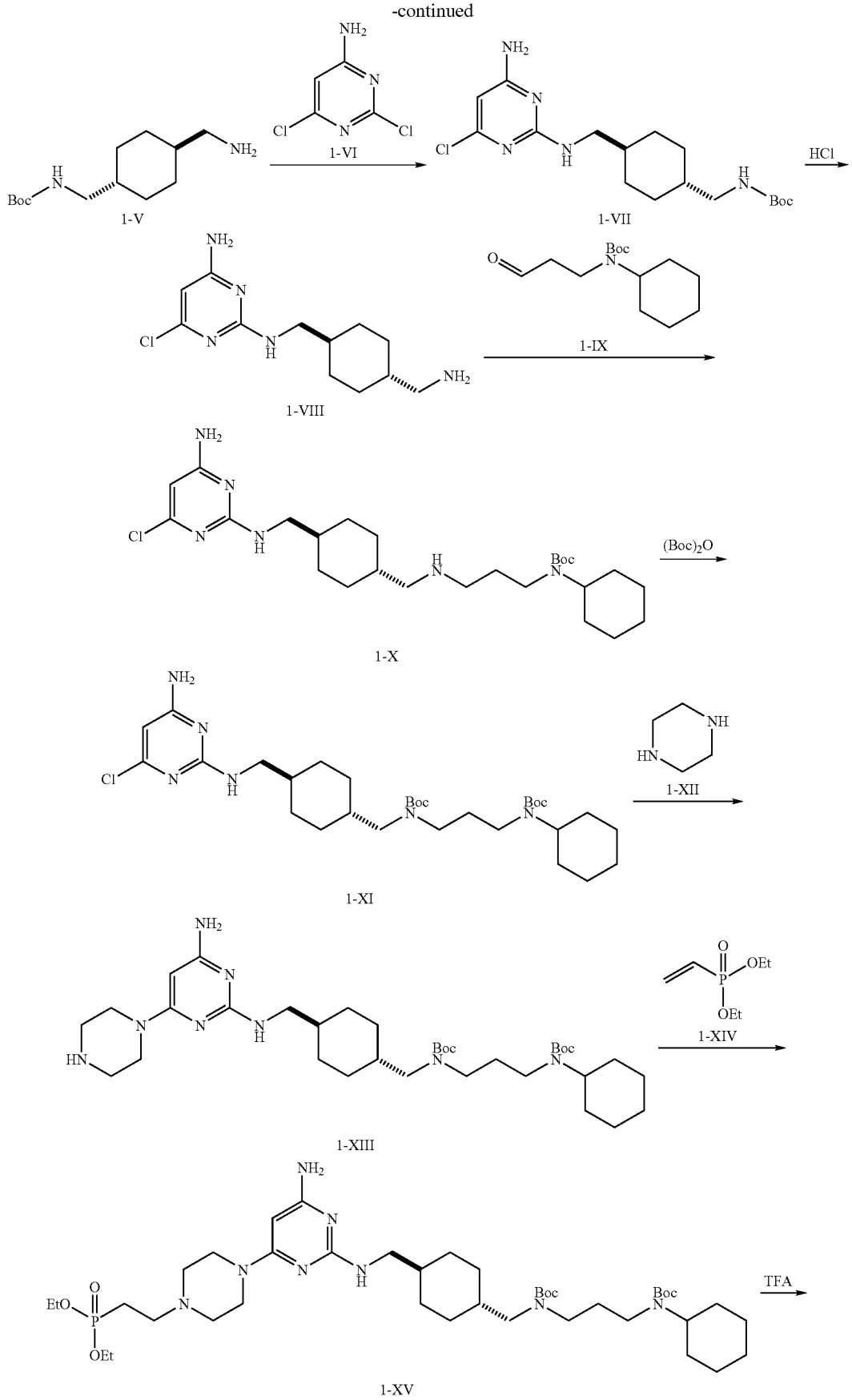

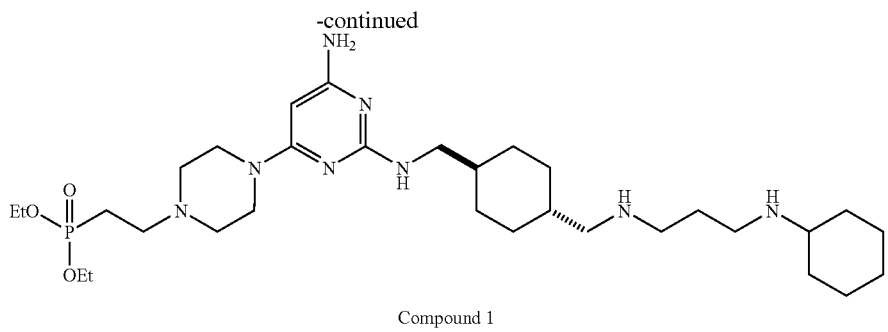

Compound 1

Water (10.0 L) and (Boc)₂O (3.33 kgg, 15.3 mol) were added to a solution of trans-4-aminomethyl-cyclohexanecarboxylic acid (compound 1-I, 2.0 kg, 12.7 mol) and sodium bicarbonate (2.67 kg, 31.8 mol). The reaction mixture was stirred at ambient temperature for 18 hours. The aqueous layer was acidified with concentrated hydrochloric acid (2.95 L, pH=2) and then filtered. The resultant solid was collected, washed three times with water (15 L), and dried in a hot box (60° C.) to give trans-4-(tert-butoxycarbonylamino-methyl)-cyclo-hexanecarboxylic acid (Compound 1-II, 3.17 kg, 97%) as a white solid. $R_f$=0.58 (EtOAc). LC-MS m/e 280 (M+Na⁺). ¹H NMR (300 MHz, CDCl₃) δ 4.58 (brs, 1H), 2.98 (t, J=6.3 Hz, 2H), 2.25 (td, J=12, 3.3 Hz, 1H), 2.04 (d, J=11.1 Hz, 2H), 1.83 (d, J=11.1 Hz, 2H), 1.44 (s, 9H), 1.35~1.50 (m, 3H), 0.89~1.03 (m, 2H). ¹³C NMR (75 MHz, CDCl₃) δ 181.31, 156.08, 79.12, 46.41, 42.99, 37.57, 29.47, 28.29, 27.96. M.p. 134.8~135.0° C.

A suspension of compound 1-II (1.0 kg, 3.89 mol) in THF (5 L) was cooled at 10° C. and triethyl amine (1.076 L, 7.78 mol) and ethyl chloroformate (0.441 L, 4.47 mol) were added below 10° C. The reaction mixture was stirred at ambient temperature for 3 hours. The reaction mixture was then cooled at 10° C. again and NH₄OH (3.6 L, 23.34 mol) was added below 10° C. The reaction mixture was stirred at ambient temperature for 18 hours and filtered. The solid was collected and washed three times with water (10 L) and dried in a hot box (60° C.) to give trans-4-(tert-butoxycarbonyl-amino-methyl)-cyclohexanecarboxylic acid amide (Compound 1-III, 0.8 kg, 80%) as a white solid. $R_f$=0.23 (EtOAc). LC-MS m/e 279, M+Na⁺. ¹H NMR (300 MHz, CD₃OD) δ 6.63 (brs, 1H), 2.89 (t, J=6.3 Hz, 2H), 2.16 (td, J=12.2, 3.3 Hz, 1H), 1.80~1.89 (m, 4H), 1.43 (s, 9H), 1.37~1.51 (m, 3H), 0.90~1.05 (m, 2H). ¹³C NMR (75 MHz, CD₃OD) δ 182.26, 158.85, 79.97, 47.65, 46.02, 39.28, 31.11, 30.41, 28.93. M.p. 221.6~222.0° C.

A suspension of compound 1-III (1.2 kg, 4.68 mol) in CH₂Cl₂ (8 L) was cooled at 10° C. and triethyl amine (1.3 L, 9.36 mol) and trifluoroacetic anhydride (0.717 L, 5.16 mol) were added below 10° C. The reaction mixture was stirred for 3 hours. After water (2.0 L) was added, the organic layer was separated and washed with water (3.0 L) twice. The organic layer was then passed through silica gel and concentrated. The resultant oil was crystallized by methylene chloride. The crystals were washed with hexane to give trans-(4-cyano-cyclohexylmethyl)-carbamic acid tent-butyl ester (Compound 1-IV, 0.95 kg, 85%) as a white crystal. $R_f$=0.78 (EtOAc). LC-MS m/e 261, M+Na⁺. ¹H NMR (300 MHz, CDCl₃) δ 4.58 (brs, 1H), 2.96 (t, J=6.3 Hz, 2H), 2.36 (td, J=12, 3.3 Hz, 1H), 2.12 (dd, J=13.3, 3.3 Hz, 2H), 1.83 (dd, J=13.8, 2.7 Hz, 2H), 1.42 (s, 9H), 1.47~1.63 (m, 3H), 0.88~1.02 (m, 2H). ¹³C NMR (75 MHz, CDCl₃) δ 155.96, 122.41, 79.09, 45.89, 36.92, 29.06, 28.80, 28.25, 28.00. M.p. 100.4~100.6° C.

Compound 1-IV (1.0 kg, 4.196 mol) was dissolved in a mixture of 1,4-dioxane (8.0 L) and water (2.0 L). To the reaction mixture were added lithium hydroxide monohydrate (0.314 kg, 4.191), Raney-nickel (0.4 kg, 2.334 mol), and 10% palladium on carbon (0.46 kg, 0.216 mol) as a 50% suspension in water. The reaction mixture was stirred under hydrogen atmosphere at 50° C. for 20 hours. After the catalysts were removed by filtration and the solvents were removed in vacuum, a mixture of water (1.0 L) and CH₂Cl₂ (0.3 L) was added. After phase separation, the organic phase was washed with water (1.0 L) and concentrated to give trans-(4-aminomethyl-cyclohexylmethyl)-carbamic acid tert-butyl ester (compound 1-V, 0.97 kg, 95%) as pale yellow thick oil. $R_f$=0.20 (MeOH/EtOAc=9/1). LC-MS m/e 243, M+H⁺. ¹H NMR (300 MHz, CDCl₃) δ 4.67 (brs, 1H), 2.93 (t, J=6.3 Hz, 2H), 2.48 (d, J=6.3 Hz, 2H), 1.73~1.78 (m, 4H), 1.40 (s, 9H), 1.35 (brs, 3H), 1.19~1.21 (m, 1H), 0.77~0.97 (m, 4H). ¹³C NMR (75 MHz, CDCl₃) δ 155.85, 78.33, 48.27, 46.38, 40.80, 38.19, 29.87, 29.76, 28.07.

A solution of compound 1-V (806 g) and Et₃N (1010 g, 3 eq) in 1-pentanol (2.7 L) was treated with compound 1-VI, 540 g, 1 eq) at 90° C. for 15 hours. TLC showed that the reaction was completed.

Ethyl acetate (1.5 L) was added to the reaction mixture at 25° C. The solution was stirred for 1 hour. The Et₃NHCl salt was filtered. The filtrate was then concentrated to 1.5 L (1/6 of original volume) by vacuum at 50° C. Then, diethyl ether (2.5 L) was added to the concentrated solution to afford the desired product 1-VII (841 g, 68% yield) after filtration at 25° C.

A solution of intermediate 1-VII (841 g) was treated with 4 N HCl/dioxane (2.7 L) in MeOH (8.1 L) and stirred at 25° C. for 15 hours. TLC showed that the reaction was completed. The mixture was concentrated to 1.5 L (1/7 of original volume) by vacuum at 50° C. Then, diethyl ether (5 L) was added to the solution slowly, and HCl salt of 1-VIII (774 g) was formed, filtered, and dried under vacuum (<10 ton). For neutralization, K₂CO₃ (2.5 kg, 8 eq) was added to the solution of HCl salt of 1-VIII in MeOH (17 L) at 25° C. The mixture was stirred at the same temperature for 3 hours (pH>12) and filtered (estimated amount of 1-VIII in the filtrate is 504 g).

Aldehyde 1-IX (581 g, 1.0 eq based on mole of 1-VII) was added to the filtrate of 1-VIII at 0-10° C. The reaction was stirred at 0-10° C. for 3 hours. TLC showed that the reaction was completed. Then, NaBH₄ (81 g, 1.0 eq based on mole of 1-VII) was added at less than 10° C. and the solution was stirred at 10-15° C. for 1 h. The solution was concentrated to get a residue, which then treated with CH₂Cl₂ (15 L). The mixture was washed with saturated aq. NH₄Cl solution (300 mL) diluted with H$_2$O (1.2 L). The CH$_2$Cl$_2$ layer was concentrated and the residue was purified by chromatography on silica gel (short column, EtOAc as mobile phase for removing other components; MeOH/28% NH$_4$OH=97/3 as mobile phase for collecting 1-X) afforded crude 1-X (841 g).

Then Et$_3$N (167 g, 1 eq) and Boc$_2$O (360 g, 1 eq) were added to the solution of 1-X (841 g) in CH$_2$Cl$_2$ (8.4 L) at 25° C. The mixture was stirred at 25° C. for 15 hours. After the reaction was completed as evidenced by TLC, the solution was concentrated and EtOAc (5 L) was added to the resultant residue. The solution was concentrated to 3 L (1/2 of the original volume) under low pressure at 50° C. Then, n-hexane (3 L) was added to the concentrated solution. The solid product formed at 50° C. by seeding to afford the desired crude product 1-XI (600 g, 60% yield) after filtration and evaporation.

To compound 1-XI (120.0 g) and piperazine (1-XII, 50.0 g, 3 eq) in 1-pentanol (360 mL) was added Et$_3$N (60.0 g, 3.0 eq) at 25° C. The mixture was stirred at 120° C. for 8 hours. Ethyl acetate (480 mL) was added to the reaction mixture at 25° C. The solution was stirred for 1 h. The Et$_3$NHCl salt was filtered and the solution was concentrated and purified by silica gel (EtOAc/MeOH=2:8) to afforded 1-XIII (96 g) in a 74% yield.

To a solution of 1-XIII (120 g) in MeOH (2.4 L) were added diethyl vinyl phosphonate (1-XIV, 45 g, 1.5 eq) at 25° C. The mixture was stirred under 65° C. for 24 hours. TLC and HPLC showed that the reaction was completed. The solution was concentrated and purified by silica gel (MeOH/CH$_2$Cl$_2$=8/92) to get 87 g of 1-XV (53% yield, purity>98%, each single impurity<1%) after analyzing the purity of the product by HPLC.

A solution of 20% TFA/CH$_2$Cl$_2$ (36 mL) was added to a solution of intermediate 1-XV (1.8 g) in CH$_2$Cl$_2$ (5 mL). The reaction mixture was stirred for 15 hours at room temperature and concentrated by removing the solvent to afford trifluoracetic acid salt of compound 1 (1.3 g).

CI-MS (M$^+$+1): 623.1.

(2) Preparation of Compound 2

Intermediate 1-XV was prepared as described in Example 1.

To a solution of 1-XV (300 g) in CH$_2$Cl$_2$ (1800 mL) was added TMSBr (450 g, 8 eq) at 10-15° C. for 1 hour. The mixture was stirred at 25° C. for 15 hours. The solution was concentrated to remove TMSBr and solvent under vacuum at 40° C. CH$_2$Cl$_2$ was added to the mixture to dissolve the residue. TMSBr and solvent were removed under vacuum again to obtain 360 g crude solid after drying under vacuum (<1 torr) for 3 hours. Then, the crude solid was washed with 7.5 L IPA/MeOH (9/1) to afford compound 2 (280 g) after filtration and drying at 25° C. under vacuum (<1 ton) for 3 hours. Crystallization by EtOH gave hydrobromide salt of compound 2 (190 g). CI-MS (M$^+$+1): 567.0.

The hydrobromide salt of compound 2 (5.27 g) was dissolved in 20 mL water and treated with concentrated aqueous ammonia (pH=9-10), and the mixture was evaporated in vacuo. The residue in water (30 mL) was applied onto a column (100 mL, 4.5×8 cm) of Dowex 50WX8 (H$^+$ form, 100-200 mesh) and eluted (elution rate, 6 mL/min). Elution was performed with water (2000 mL) and then with 0.2 M aqueous ammonia. The UV-absorbing ammonia eluate was evaporated to dryness to afford ammonia salt of compound 2 (2.41 g). CI-MS (M$^+$+1): 567.3.

The ammonia salt of compound 2 (1.5 g) was dissolved in water (8 mL) and alkalified with concentrated aqueous ammonia (pH=11), and the mixture solution was applied onto a column (75 mL, 3×14 cm) of Dowex 1×2 (acetate form, 100-200 mesh) and eluted (elution rate, 3 mL/min). Elution was performed with water (900 mL) and then with 0.1 M acetic acid. The UV-absorbing acetic acid eluate was

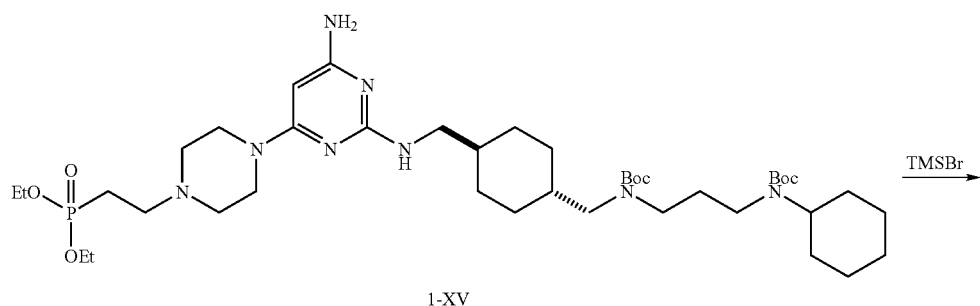

1-XV

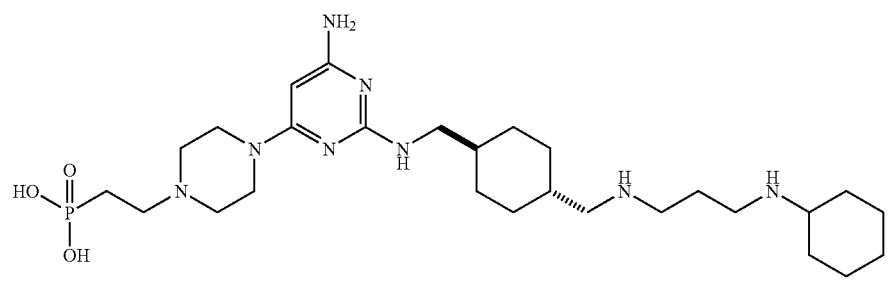

Compound 2 evaporated, and the residue was codistilled with water (5×50 mL) to afford compound 2 (1.44 g). CI-MS (M++1): 567.4.

(3) Preparation of Compound 3

Compound 3-III (505 mg) was added to a solution of intermediate 1-XIII (500 mg) in MeOH (4 mL). The solution was stirred at 45° C. for 24 hours. The solution was concentrated

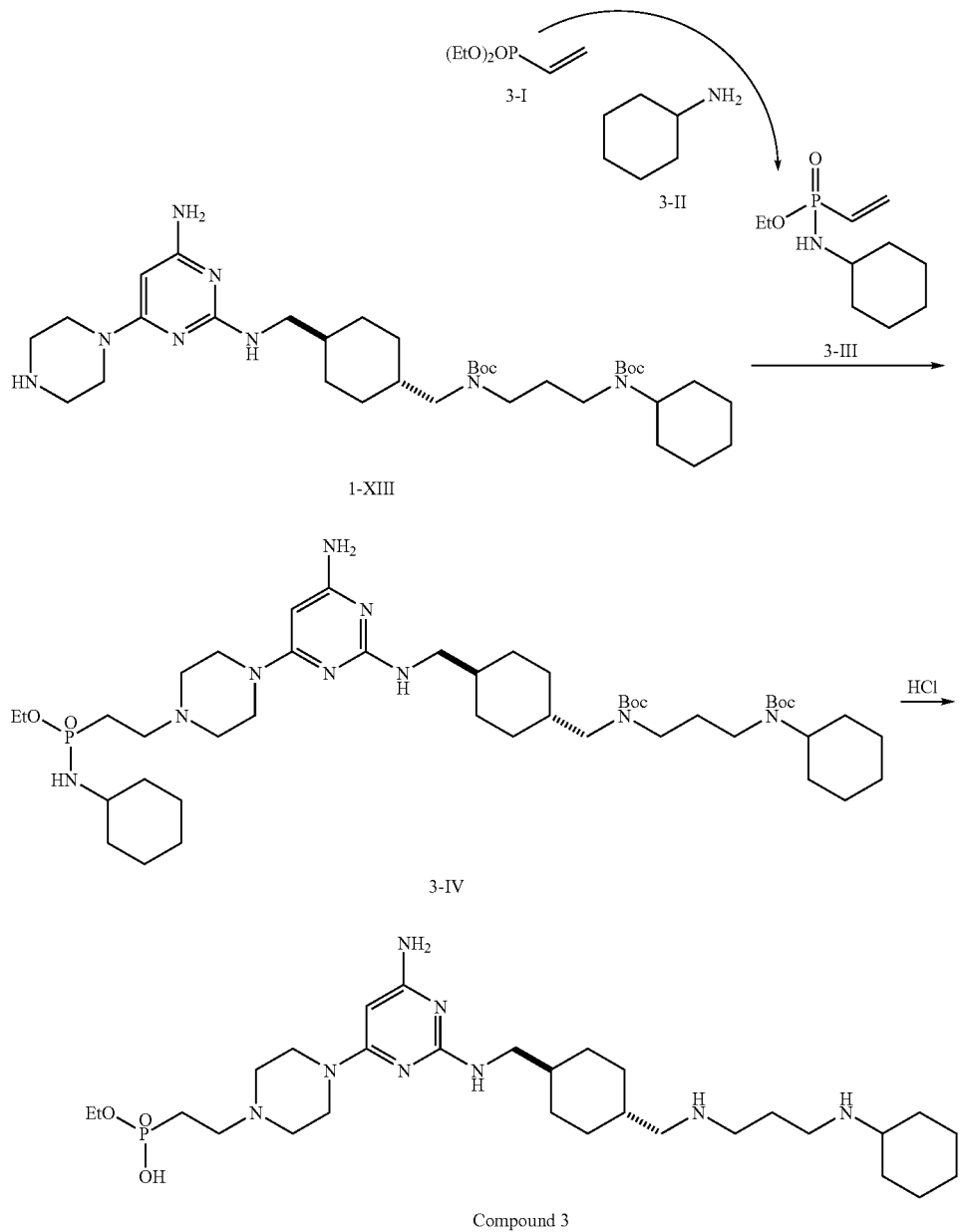

Intermediate 1-XIII was obtained during the preparation of compound 1.

To a solution of diethyl vinyl phosphonate (3-I, 4 g) in CH$_2$Cl$_2$ (120 mL) was added oxalyl chloride (15.5 g, 5 eq) and the mixture was stirred at 30° C. for 36 hours. The mixture were concentrated under vacuum on a rotatory evaporated to give quantitatively the corresponding phosphochloridate, which was added to a mixture of cyclohexyl amine (3-II, 5.3 g, 2.2 eq), CH$_2$Cl$_2$ (40 mL), and Et$_3$N (6.2 g, 2.5 eq). The mixture was stirred at 35° C. for 36 hours, and then was washed with water. The organic layer was dried (MgSO$_4$), filtered, and evaporated to afford 3-III (4.7 g, 85% yield) as brown oil.

and the residue was purified by column chromatography on silica gel (EtOAc/MeOH=4:1) to afford intermediate 3-IV (420 mg) in a 63% yield.

A solution of HCl in ether (5 mL) was added to a solution of intermediate 3-IV (420 mg) in CH$_2$Cl$_2$ (1.0 mL). The reaction mixture was stirred for 12 hours at room temperature and concentrated by removing the solvent. The resultant residue was washed with ether to afford hydrochloride salt of compound 3 (214 mg).

CI-MS (M$^+$+1): 595.1.

(4) Preparation of Compound 4

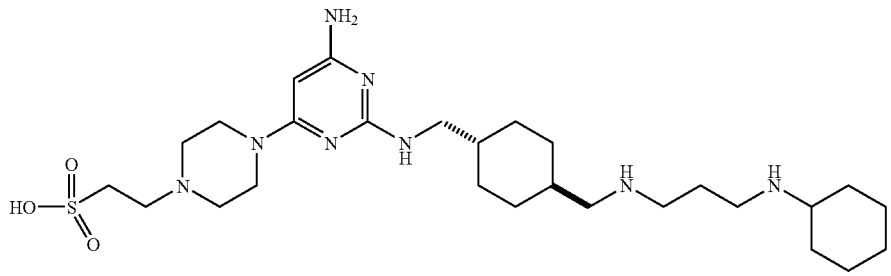

Compound 4

Compound 4 was prepared in the same manner as that described in Example 2 except that sodium 2-bromoethanesulfonate in the presence of $Et_3N$ in DMF at 45° C. was used instead of diethyl vinyl phosphonate. Deportations of amino-protecting group by hydrochloride to afford hydrochloride salt of compound 4.

CI-MS ($M^+$+1): 567.3

(5) Preparation of Compound 5

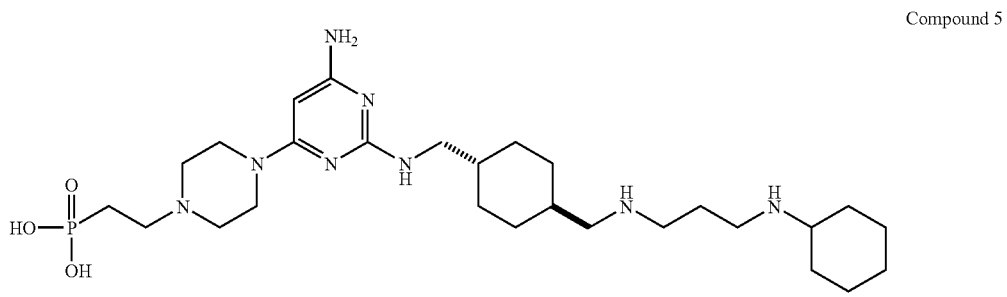

Compound 5

Compound 5 was prepared in the same manner as that described in Example 2 except that diethyl-1-bromopropylphosphonate in the presence of $K_2CO_3$ in $CH_3CN$ was used instead of diethyl vinyl phosphonate.

CI-MS ($M^+$+1): 581.4

(6) Preparation of Compound 6

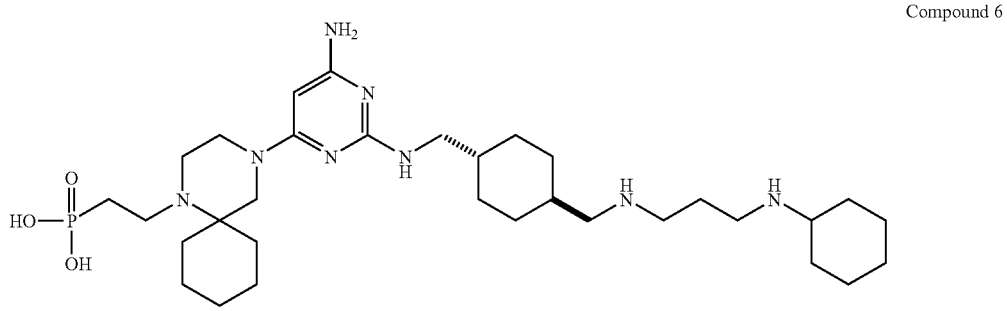

Compound 6

Compound 6 was prepared in the same manner as that described in Example 5 except that 1,4-diaza-spiro[5.5]undecane dihydrochloride was used instead of piperazine.

CI-MS ($M^+$+1): 649.5

(7) Preparation of Compound 7
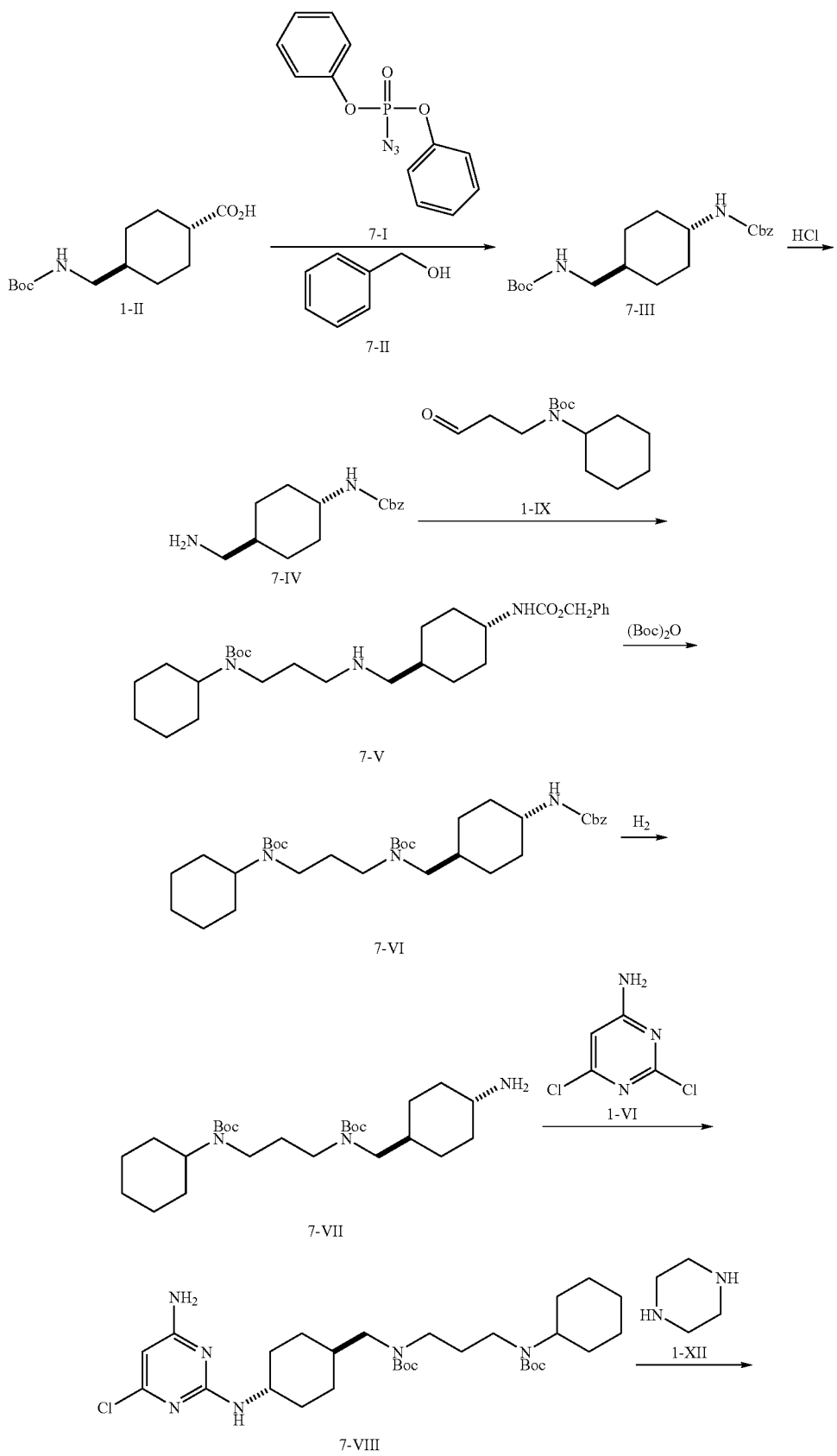

-continued

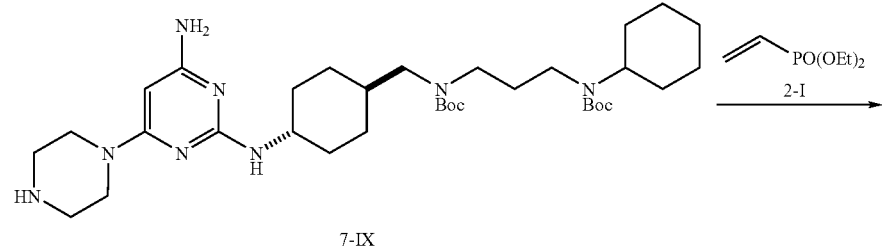

7-IX

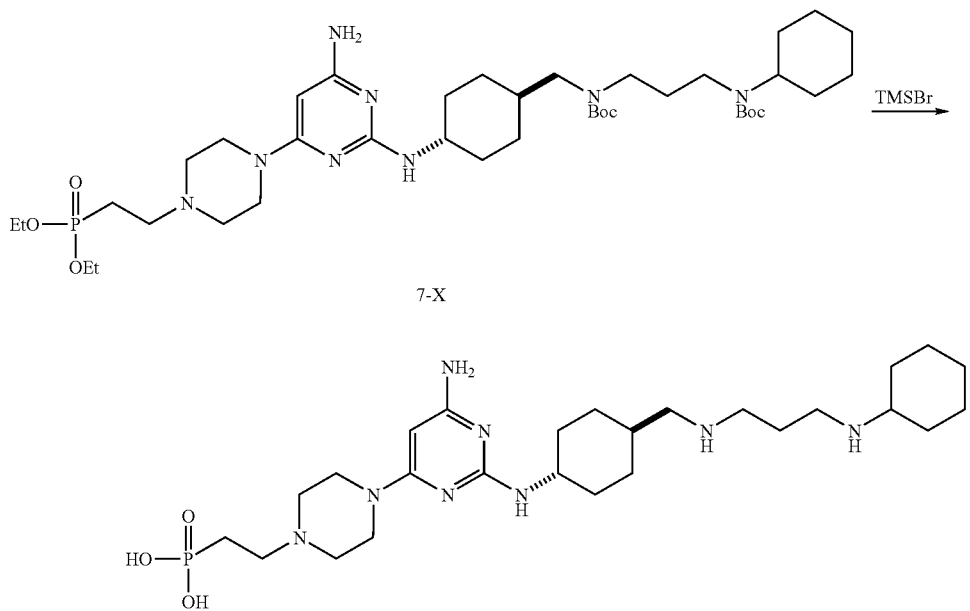

7-X

Compound 7

Intermediate 1-II was prepared as described in Example 1.

To a suspension of the intermediate 1-II (31.9 g) in toluene (150 mL) were added phosphorazidic acid diphenyl ester (7-I, 32.4 g) and $Et_3N$ (11.9 g) at 25° C. for 1 hour. The reaction mixture was stirred at 80° C. for 3 hours and then cooled to 25° C. After benzyl alcohol (7-II, 20 g) was added, the reaction mixture was stirred at 80° C. for additional 3 hours and then warmed to 120° C. overnight. It was then concentrated and dissolved again in EtOAc and $H_2O$. The organic layer was collected. The aqueous layer was extracted with EtOAc. The combined organic layers were washed with 2.5 N HCl, saturated aqueous $NaHCO_3$ and brine, dried over anhydrous $MgSO_4$, filtered, and concentrated. The residue thus obtained was purified by column chromatography on silica gel (EtOAc/Hexane=1:2) to give Intermediate 7-III (35 g) in a 79% yield.

A solution of intermediate 7-III (35 g) treated with 4 N HCl/dioxane (210 mL) in MeOH (350 mL) was stirred at room temperature overnight. After ether (700 mL) was added, the solution was filtered. The solid was dried under vacuum. $K_2CO_3$ was added to a suspension of this solid in $CH_3CN$ and iso-propanol at room temperature for 10 minutes. After water was added, the reaction mixture was stirred at room temperature for 2 hours, filtered, dried over anhydrous $MgSO_4$, and concentrated. The resultant residue was purified by column chromatography on silica gel (using $CH_2Cl_2$ and MeOH as an eluant) to give intermediate 7-IV (19 g) in a 76% yield.

Intermediate 1-IX (21 g) was added to a solution of intermediate 7-IV (19 g) in $CH_2Cl_2$ (570 mL). The mixture was stirred at 25° C. for 2 hours. $NaBH(OAc)_3$ (23 g) was then added at 25° C. overnight. After the solution was concentrated, a saturated aqueous $NaHCO_3$ solution was added to the resultant residue. The mixture was then extracted with $CH_2Cl_2$. The solution was concentrated and the residue was purified by column chromatography on silica gel (using EtOAc and MeOH as an eluant) to afford intermediate 7-V (23.9 g) in a 66% yield.

A solution of intermediate 7-V (23.9 g) and $Boc_2O$ (11.4 g) in $CH_2Cl_2$ (200 mL) was added to $Et_3N$ (5.8 mL) at 25° C. for overnight. The solution was then concentrated and the resultant residue was purified by column chromatography on silica gel (using EtOAc and Hexane as an eluant) to give intermediate 7-VI (22 g) in a 77% yield. 10% Pd/C (2.2 g) was added to a suspension of intermediate 7-VI (22 g) in MeOH (44 mL). The mixture was stirred at ambient temperature under hydrogen atmosphere overnight, filtered, and concentrated. The residue thus obtained was purified by column chromatography on silica gel (using EtOAc and MeOH as an eluant) to afford intermediate 7-VII (16.5 g) in a 97% yield.

Intermediate 7-VII (16.5 g) and $Et_3N$ (4.4 mL) in 1-pentanol (75 mL) was allowed to react with 2,4-dichloro-6-aminopyrimidine (1-VI, 21 g) at 120° C. overnight. The solvent was then removed and the residue was purified by column chromatography on silica gel (using EtOAc and hexane as an eluant) to afford intermediate 7-VIII (16.2 g) in a 77% yield.

A solution of intermediate 7-VIII (16.2 g) and piperazine (1-XII, 11.7 g) in 1-pentanol (32 mL) was added to Et₃N (3.3 mL) at 120° C. overnight. After the solution was concentrated, the residue was treated with water and extracted with CH₂Cl₂. The organic layer was collected and concentrated. The residue thus obtained was purified by column chromatography on silica gel (using EtOAc/MeOH to 28% NH₄OH/ MeOH as an eluant) to afford Intermediate 7-IX (13.2 g) in a 75% yield.

Diethyl vinyl phosphonate (2-I) was treated with 7-IX as described in Example 3 to afford hydrobromide salt of compound 7.

CI-MS (M$^+$+1): 553.3

(8) Preparation of Compound 8

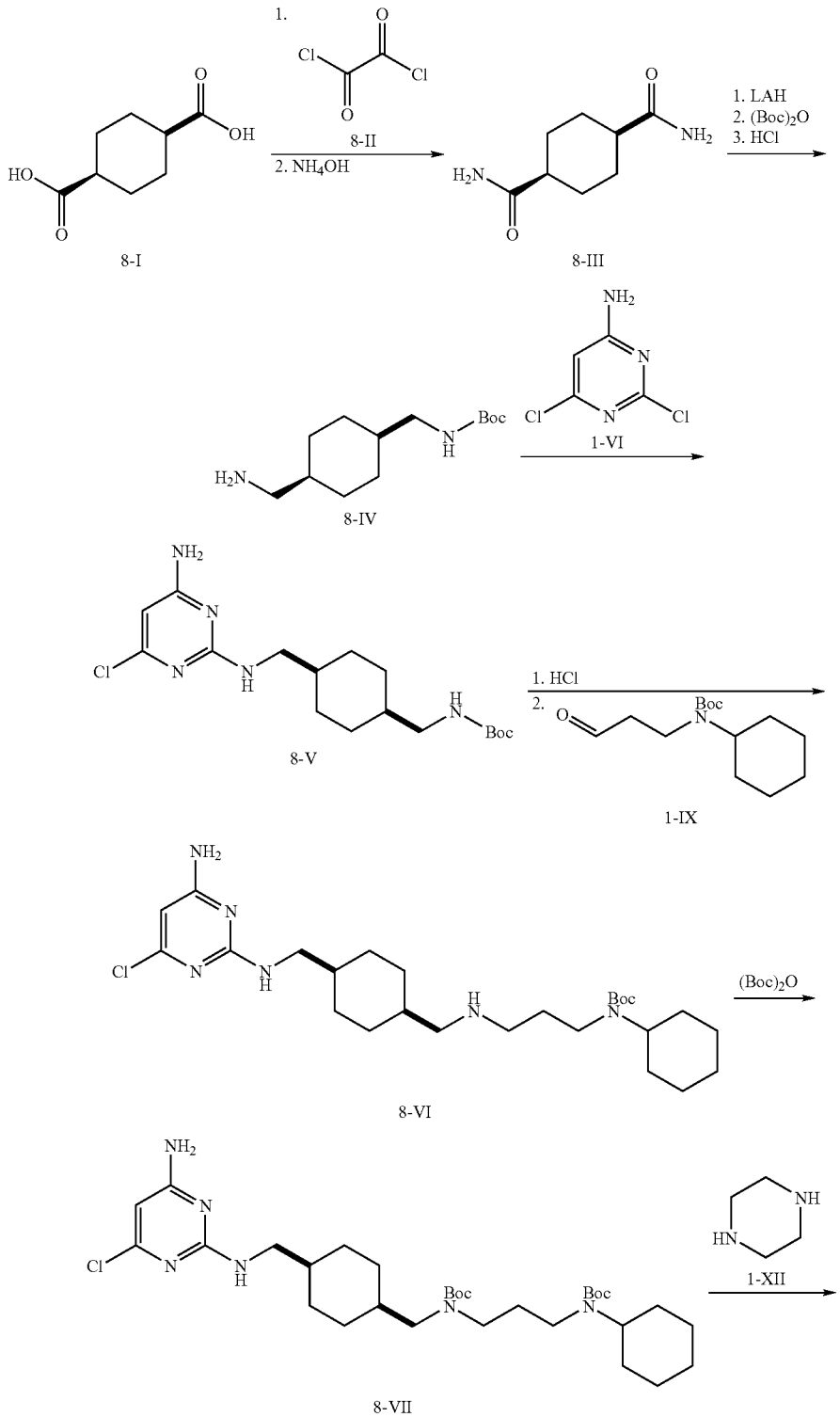

-continued

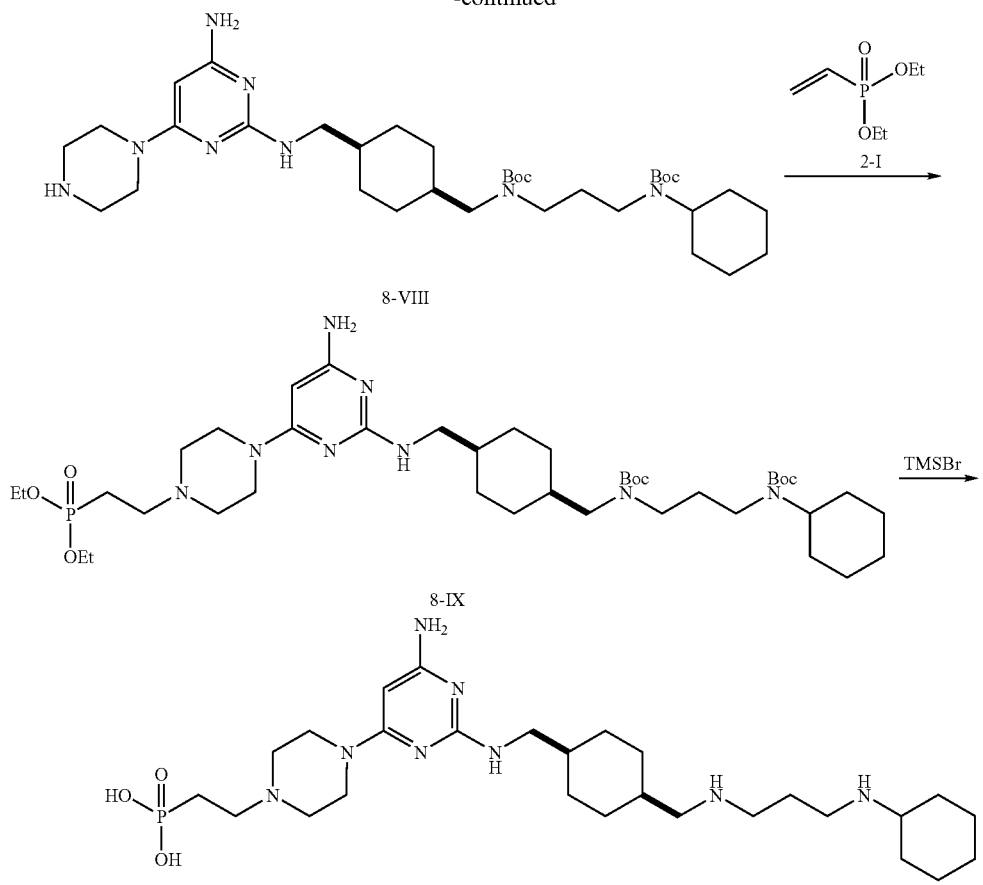

Compound 8

Cis-1,4-cyclohexanedicarboxylic acid (8-I, 10 g) in THF (100 ml) was added oxalyl chloride (8-II, 15.5 g) at 0° C. and then DMF (few drops). The mixture was stirred at room temperature for 15 hours. The solution was concentrated and the residue was dissolved in THF (100 ml). The mixture solution was added to ammonium hydroxide (80 ml) and stirred for 1 hour. The solution was concentrated and filtration to afford crude product 8-III (7.7 g).

Compound 8-III (7.7 g) in THF (200 ml) was slowly added to LiAlH$_4$ (8.6 g) in THF (200 ml) solution at 0° C. The mixture solution was stirred at 65° C. for 15 hours. NaSO$_4$.10H$_2$O was added at room temperature and stirred for 1 hours. The resultant mixture was filtered to get filtrate and concentrated. The residue was dissolved in CH$_2$Cl$_2$ (100 ml). Et$_3$N (27 g) and (Boc)$_2$O (10 g) were added at room temperature. The solution was stirred for 15 h, and then concentrated to get resultant residue. Ether was added to the resultant residue. Filtration and drying under vacuum afforded solid crude product 8-IV (8.8 g).

A solution of compound 8-IV (1.1 g) and Et$_3$N (1.7 g) in 1-pentanol (10 ml) was reacted with 2,4-dichloro-6-aminopyrimidine (1-VI, 910 mg) at 90° C. for 15 hours. TLC showed that the reaction was completed. Ethyl acetate (10 mL) was added to the reaction mixture at 25° C. The solution was stirred for 1 hour. The Et$_3$NHCl salt was removed. The filtrate was concentrated and purified by silica gel (EtOAc/Hex=1:2) to afford the desired product 8-V (1.1 g, 65% yield).

A solution of intermediate 8-V (1.1 g) was treated with 4 N HCl/dioxane (10 ml) in MeOH (10 ml) and stirred at 25° C. for 15 hours. TLC showed that the reaction was completed. The mixture was concentrated, filtered, and dried under vacuum (<10 ton). For neutralization, K$_2$CO$_3$ (3.2 g) was added to the solution of HCl salt in MeOH (20 ml) at 25° C. The mixture was stirred at the same temperature for 3 hours (pH>12) and filtered. Aldehyde 1-IX (759 mg) was added to the filtrate at 0-10° C. The reaction was stirred at 0-10° C. for 3 hours. TLC showed that the reaction was completed. Then, NaBH$_4$ (112 mg) was added at less than 10° C. and the solution was stirred at 10-15° C. for 1 hour. The solution was concentrated to get a residue, which was then treated with CH$_2$Cl$_2$ (10 mL). The mixture was washed with saturated NH$_4$Cl (aq) solution. The CH$_2$Cl$_2$ layer was concentrated and the residue was purified by chromatography on silica gel (MeOH/28% NH$_4$OH=97/3) to afford intermediate 8-VI (1.0 g, 66% yield).

Et$_3$N (600 mg) and Boc$_2$O (428 mg) were added to the solution of 8-VI (1.0 g) in CH$_2$Cl$_2$ (10 ml) at 25° C. The mixture was stirred at 25° C. for 15 hours. TLC showed that the reaction was completed. The solution was concentrated and purified by chromatography on silica gel (EtOAc/Hex=1:1) to afford intermediate 8-VII (720 mg, 60% yield).

To a solution compound 8-VII (720 mg) and piperazine (1-XII, 1.22 g) in 1-pentanol (10 mL) was added Et$_3$N (1.43 g) at 25° C. The mixture was stirred at 120° C. for 24 hours. TLC showed that the reaction was completed. Ethyl acetate (20 mL) was added at 25° C. The solution was stirred for 1 hour. The Et$_3$NHCl salt was removed and the solution was concentrated and purified by silica gel (EtOAc/MeOH=2:8) to afford 8-VIII (537 mg) in 69% yield.

To a solution of 8-VIII (537 mg) in MeOH (11 ml) was added diethyl vinyl phosphonate (2-I, 201 mg) at 25° C. The mixture was stirred under 65° C. for 24 hours. TLC and HPLC showed that the reaction was completed. The solution was concentrated and purified by silica gel (MeOH/CH$_2$Cl$_2$=1:9) to get 8-IX (380 mg) in a 57% yield.

To a solution of 8-IX (210 mg) in CH$_2$Cl$_2$ (5 ml) was added TMSBr (312 mg) at 10-15° C. for 1 hour. The mixture was stirred at 25° C. for 15 hours. The solution was concentrated to remove TMSBr and solvent under vacuum at 40° C., then, CH$_2$Cl$_2$ was added to dissolve the residue. Then TMSBr and solvent were further removed under vacuum and CH$_2$Cl$_2$ was added for four times repeatedly. The solution was concentrated to get hydrobromide salt of compound 8 (190 mg).

CI-MS (M$^+$+1): 566.9

(9) Preparation of Compound 9

Intermediate 1-XIII was prepared as described in Example 1.

To a solution of vinylphosphonic acid (9-I, 550 mg) in dry CH$_2$Cl$_2$ (17 mL) was slowly added oxalyl chloride (3.9 g) and DMF (0.4 mL) at 0° C. The mixture was refluxed for 3 hours, and concentrated to give quantitatively the corresponding phosphochloridate. The phosphochloridate was added to a mixture of 2,2-dimethyl-1,3-propanediol (9-II, 530 mg), dry CH$_2$Cl$_2$ (17 mL), and Et$_3$N (3.1 g) at −70° C. The mixture was slowly warmed to room temperature and stirred at for 15 hours. It was then washed with water. The organic layer was dried (MgSO$_4$), filtered, and evaporated. The residue was purified by column chromatography on silica gel (EtOAc/MeOH=9:1) to afford 9-III (65 mg, 7% yield) as brown oil.

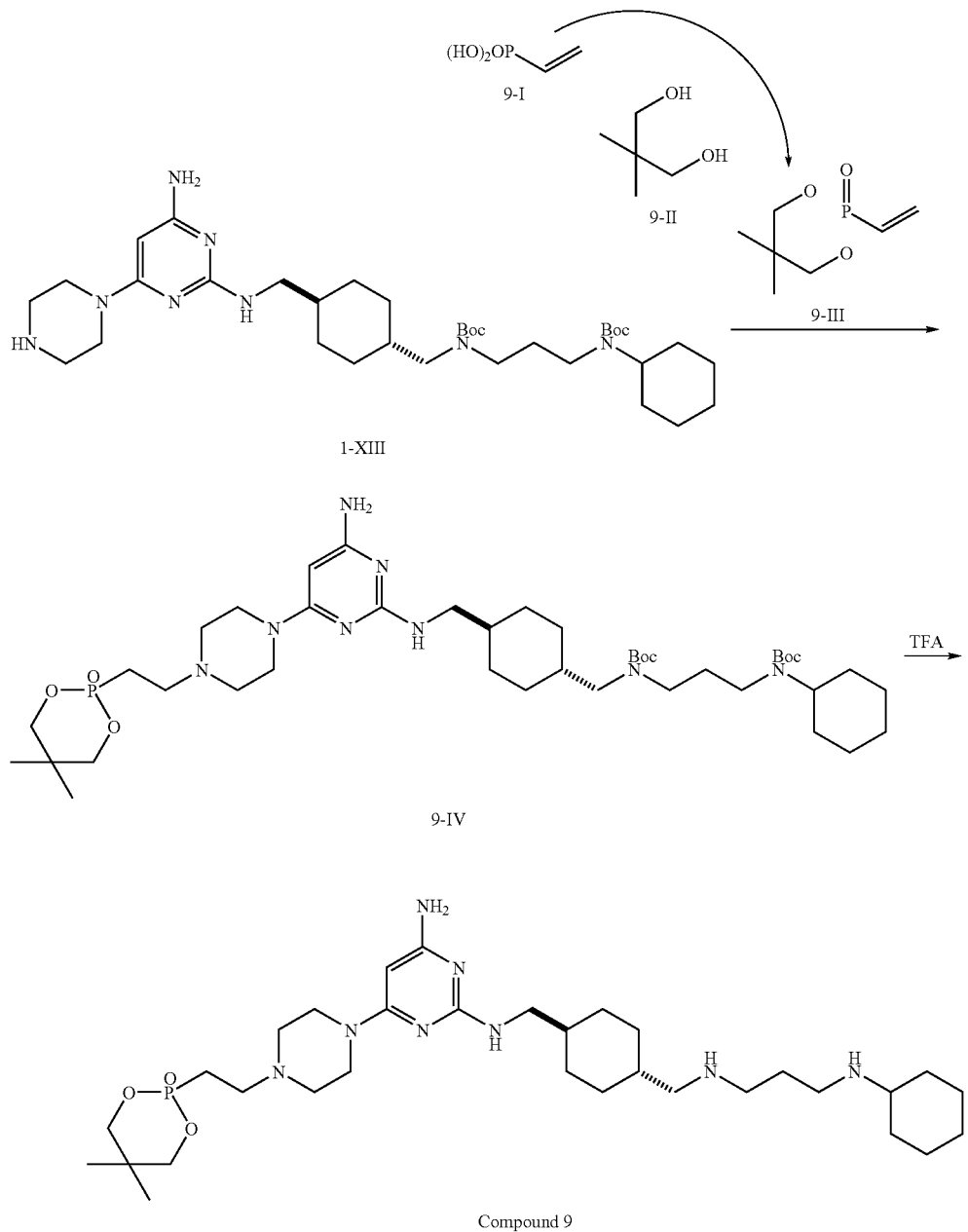

Compound 9-III (65 mg) was added to a solution of intermediate 1-XIII (202 mg) in MeOH (4 mL). The solution was stirred at 65° C. for 24 hours. The solution was concentrated and the residue was purified by column chromatography on silica gel (CH$_2$Cl$_2$/MeOH=9:1) to afford intermediate 9-IV (147 mg) in a 48% yield.

A solution of 20% TFA/CH$_2$Cl$_2$ (3 mL) was added to a solution of intermediate 9-IV (147 mg) in CH$_2$Cl$_2$ (2.0 mL). The reaction mixture was stirred for 12 hours at room temperature and concentrated to afford trifluoracetic acid salt of compound 9 (267 mg).

CI-MS (M$^+$+1): 635.4

(10) Preparation of Compound 10

Compound 10 was prepared in the same manner as that described in Example 9 except that 2-aminobenzyl alcohol was used instead of 2,2-dimethyl-1,3-propanediol.

CI-MS (M$^+$+1): 654.4

(11) Preparation of Compound 11

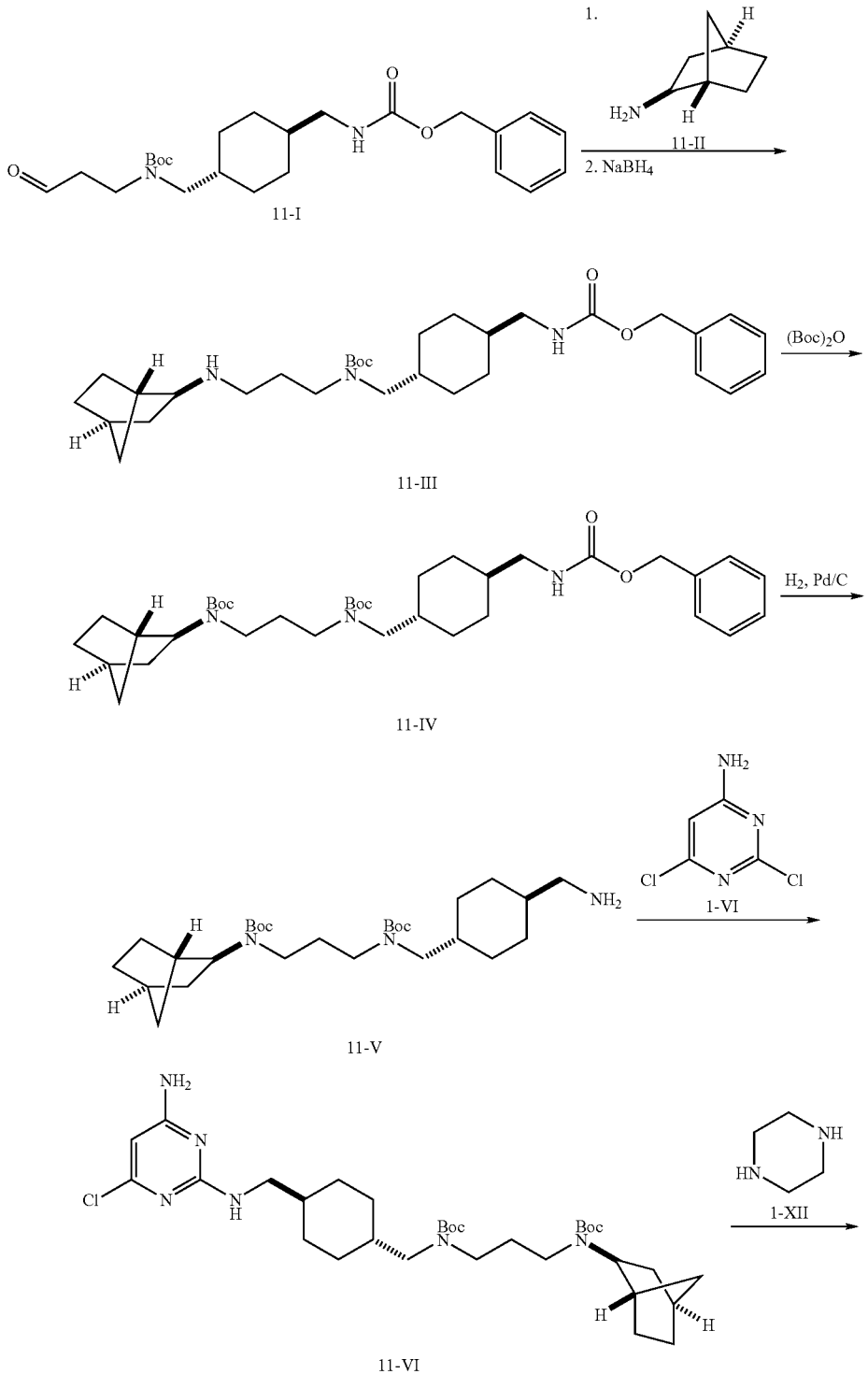

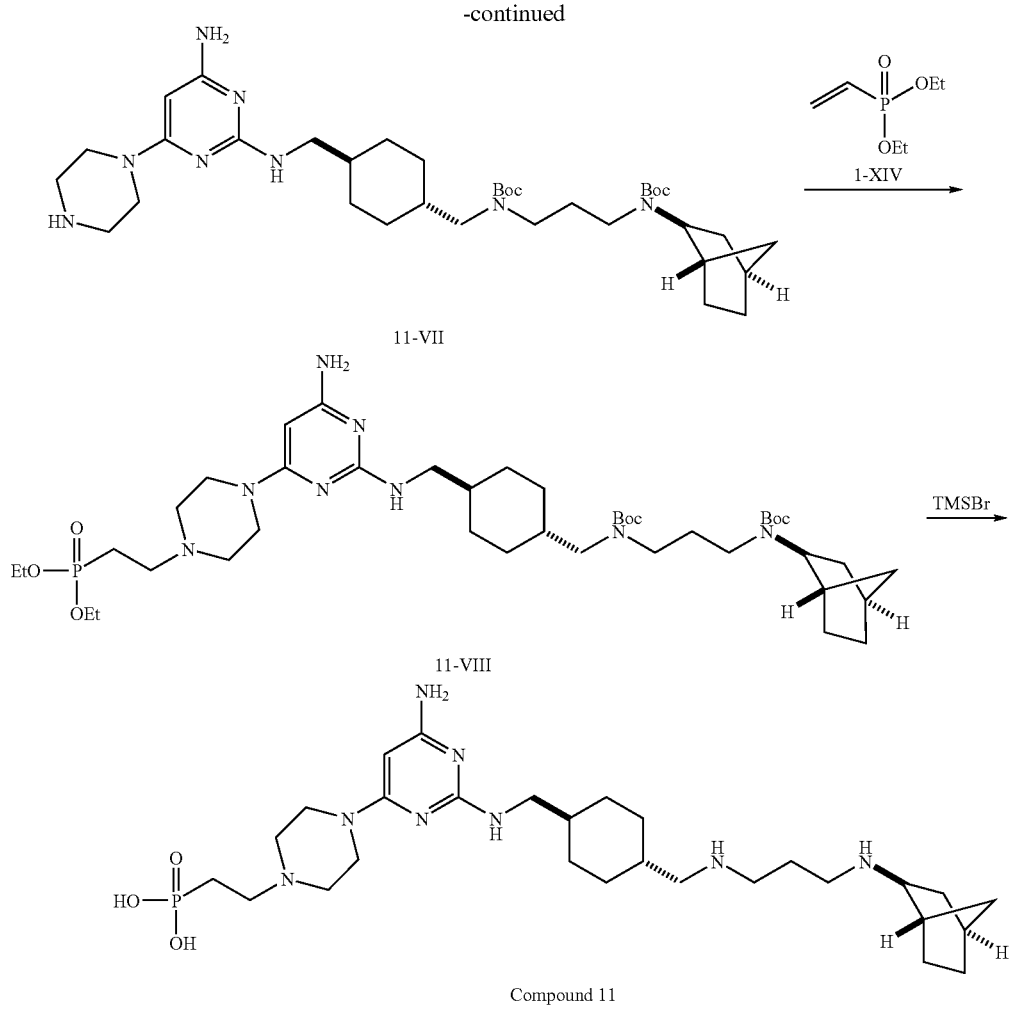

Compound 11

11-I (1000 mg) and exo-2-aminonorbornane (11-II, 257 mg) in MeOH (10 mL) was stirred at 0° C. for 3 hours. NaBH$_4$ (87.5 mg) was then added at 0° C. during a period of 1 hour. The solution was concentrated, quenched with NH$_4$Cl (aq), and extracted with CH$_2$Cl$_2$. The organic layers were combined, dried with anhydrous MgSO$_4$, and concentrated to give a residue, which was purified by chromatography on silica gel (MeOH/28% NH$_4$OH=97/3) to afford intermediate 11-III (1000 mg, 82% yield).

A solution of intermediate 11-III (1000 mg), Et$_3$N (210 mg) and Boc$_2$O (455 mg) in CH$_2$Cl$_2$ (10 mL) was stirred at 25° C. for 15 hours. The solution was concentrated and purified by chromatography on silica gel (EtOAcA/Hexane=1/1) to afford intermediate 11-IV (907 mg, 76% yield).

A solution of intermediate 11-IV (907 mg) and Pd/C (20 mg) in MeOH (10 mL) was stirred under H$_2$ (balloon) at 25° C. for 18 hours. The solution was filtered through a celite column and MeOH was removed to afford intermediate 11-V (740 mg).

Et$_3$N (454 mg) was added to a solution of intermediate 11-V (740 mg) and 2,4-dichloro-6-aminopyrimidine (1-VI, 246 mg) in 1-pentanol (10 mL). The reaction mixture was stirred at 120° C. for 15 hours and concentrated under vacuum. The resultant residue was purified by chromatography on silica gel (EtOAc/Hexane=1/2) to afford intermediate 11-VI (420 mg, 45% yield).

To compound 11-VI (1.7 g) and piperazine (1-XII, 1.4 g, 6 eq) in 1-pentanol (30 mL) was added Et$_3$N (1.66 g, 6.0 eq) at 25° C. The mixture was stirred at 120° C. for 15 hours. The solution was concentrated and purified by silica gel (EtOAc/ MeOH=8:2) to afford 11-VII (1.5 g) in a 82% yield.

To a solution of 11-VII (1.5 g) in MeOH (30 mL) was added diethyl vinyl phosphonate (1-XIV, 0.556 g, 1.5 eq) at 25° C. The mixture was stirred under 65° C. for 24 hours. TLC and HPLC showed that the reaction was completed. The solution was concentrated and purified by silica gel (MeOH/ CH$_2$Cl$_2$=8/92) to get 1.1 g of 11-VIII in a 59% yield.

To a solution of 11-VIII (1.0 g) in CH$_2$Cl$_2$ (5 mL) was added TMSBr (1.46 g, 8 eq) at 10-15° C. for 1 hour. The mixture was stirred at 25° C. for 15 hours. The solution was concentrated to remove TMSBr and the solvent under vacuum at 40° C. CH$_2$Cl$_2$ was added to the mixture to dissolve the residue. TMSBr and the solvent were removed under vacuum again to obtain a crude solid, which was washed with IPA/MeOH (9/1) to afford compound 11 after filtration and drying at 25° C. under vacuum (<1 ton) for 3 hours. Crystallization in EtOH gave hydrobromide salt of compound 11 (530 mg).

CI-MS (M$^+$+1): 579.4

(12) Preparation of Compound 12

Compound 12 was prepared in the same manner as that described in Example 11 except that cyclohexylmethanamine was used instead of exo-2-aminonorborane.

CI-MS (M$^+$+1): 581.4

Lyophilization (1) Preparation of Aqueous Solution

In a glass beaker, 3.00 g of mannitol and 0.7622 g of a test compound (in the HBr salt form) were dissolved in less than 100 mL of 0.2% (w/v) NaCl solution. The solution was transferred to a 100 mL volumetric flask. The beaker was rinsed with 0.2% NaCl solution and the solution was transferred to the volumetric flask. The volume of the solution in the volumetric flask was adjusted to 100 mL with 0.2% NaCl solution. The solution thus prepared contained 5 mg/mL the test compound (free-base), 3% (w/v) mannitol, and 0.2% (w/v) NaCl. The resulting solution was first pre-filtered and then filtered through a sterilized 0.22 μm Millipore Durapore™ microfilter. The Sterile-filtered solution was used for lyophilization.

In similar manners, a solution containing 5 mg/mL the test compound, 3% (w/v) mannitol, and 0.3% (w/v) NaCl and a solution containing 5 mg/mL the test compound, 3% (w/v) mannitol, and 0.4% (w/v) NaCl were prepared.

(2) Lyophilization of Solution

Solutions were transferred to vials. The vials were cooled to and equilibrated at 20° C. It was further cooled to 5° C. over 20 min and kept at that temperature for 30 min. Then, it was cooled to −45° C. over 180 min and kept at that temperature for 4 hr. Vacuum at 133 Oar was applied to the vials. Under the vacuum, the temperature of the vials was allowed to rise to −38° C. over 60 min and kept at that temperature for 6 hours. Then, it was vacuumed at −29° C. for 5 hr and −27° C. for 15 hr.

While the vacuum was maintained at 133 Oar, the temperature of the vials was allowed to rise to −3° C. over 60 min. After 6 hours, the temperature was allowed to rise to 5° C. over 60 min. The vials were vacuumed at 48 Oar for 99 h and then sealed under nitrogen.

(3) Scale-Up Preparation of Lyophilized Compositions

2 L of a solution containing 5 mg/ml of a test compound, 3% (w/v) mannitol, and 0.2% (w/v) NaCl was prepared. It was filtered through a Millipak 20, 0.22 μm PVDF filter. The solution was transferred to 10 mL Schott Type 1 clear glass vials and lyophilized under the conditions listed in the following table:

|  | temperature | pressure | time |
| --- | --- | --- | --- |
| Cooling | 20° C. | normal | N/A |
| Cooling | 5° C. | normal | 50 min |
| Cooling | 5° C. to −45° C. | normal | 3 hr |
| Freezing | −45° C. | normal | 6 hr |
| Drying | −45° C. to −38° C. | 133 μbar | 1 hr |
| Drying | −38° C. | 133 μbar | 3 hr |
| Drying | −38° C. to −29° C. | 133 μbar | 2 hr |
| Drying | −29° C. | 133 μbar | 5 hr |
| Drying | −29° C. to −27° C. | 133 μbar | 2 hr |
| Drying | −27° C. | 133 μbar | 20 hr |
| Drying | −27° C. to −3° C. | 133 μbar | 1 hr |
| Drying | −3° C. | 133 μbar | 3 hr |
| Drying | −3° C. to 12° C. | 133 μbar | 1 hr |
| Drying | 12° C. | 133 μbar | 12 hr |
| Drying | 12° C. to 5° C. | 133 μbar | 0.5 hr |
| Drying | 5° C. | 48 μbar | 99 hr |

The vials were sealed under nitrogen with Helvoet Omniflex Rubber Lyostoppers.

Stability Studies

The vials were stored at 5° C./ambient relative humidity, 25° C./60% relative humidity, or 40° C./75% relative humidity for 1, 2, 3, or 6 months. Compared with that obtained immediately after lyophilization, the compositions stored for 1, 2, 3, and 6 moths had little or no change in respect of its compound content, moisture content, appearance, and pH. The reconstitution time, although increased, was still very short, i.e., around 30-40 second.

Other Embodiments

All of the features disclosed in this specification may be combined in any combination. An alternative feature serving the same, equivalent, or similar purpose may replace each feature disclosed in this specification. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pharmaceutical kit comprising:
   a lyophilized preparation of a compound of the following formula:

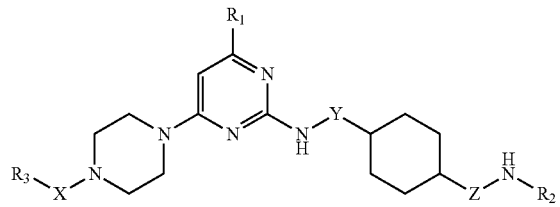

wherein
   each of X, Y, and Z, independently, is $C_{1-5}$ alkylene or deleted;
   $R_1$ is H, $C_{1-5}$ alkyl, OH, or $NH_2$;
   $R_2$ is $C_{3-10}$ cycloalkyl or ($C_{1-5}$ alkyl)-NH—($C_{3-10}$ cycloalkyl); and
   $R_3$ is $P(=O)(OH)_2$, $P(=O)(OH)(OC_{1-5}$ alkyl), $P(=O)(OC_{1-5}$ alkyl)$_2$, $S(=O)_2(OH)$, $S(=O)_2C_{1-5}$ alkyl, or $S(=O)_2Ph$; and
   a sealed container,
wherein the lyophilized preparation is disposed in the sealed container.

2. The pharmaceutical kit of claim 1, wherein X is —CH$_2$—, —CH$_2$CH$_2$— or —CH$_2$CH$_2$CH$_2$— and Y is —CH$_2$ or deleted and Z is —CH$_2$—.

3. The pharmaceutical kit of claim 1, wherein R$_1$ is NH$_2$; and R$_2$ is (C$_{1-5}$ alkyl)-NH—(C$_{3-10}$ cycloalkyl).

4. The pharmaceutical kit of claim 1, wherein R$_3$ is P(=O)(OH)$_2$, P(=O)(OH)(OCH$_2$CH$_3$), P(=O)(OCH$_2$CH$_3$)$_2$, S(=O)$_2$OH, S(=O)$_2$CH$_3$, or S(=O)$_2$Ph.

5. The pharmaceutical kit of claim 1, wherein the lyophilized compound is one of the compounds shown below:

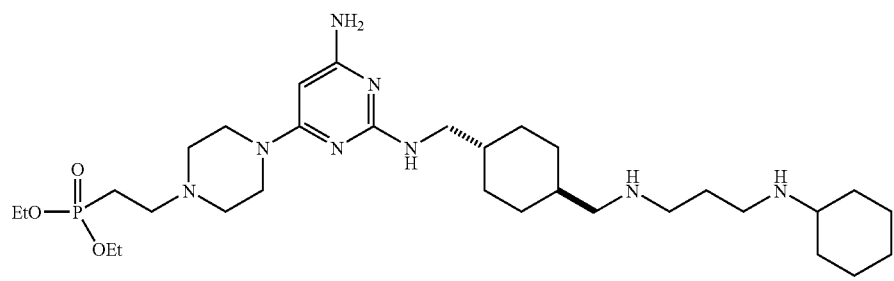

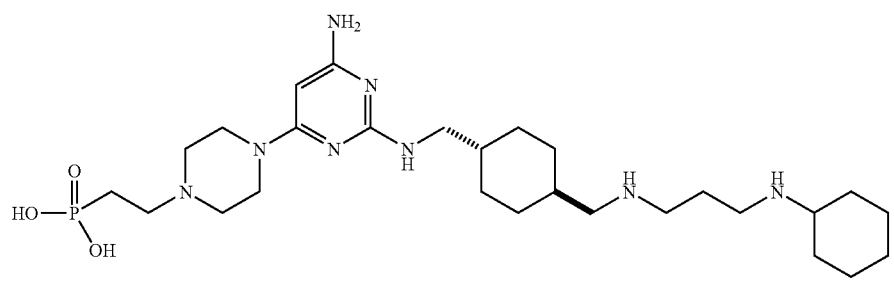

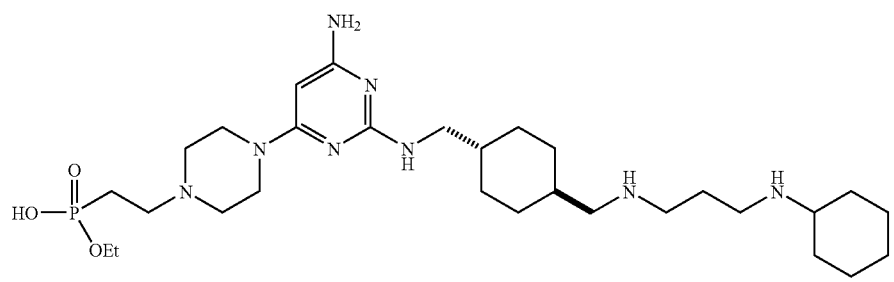

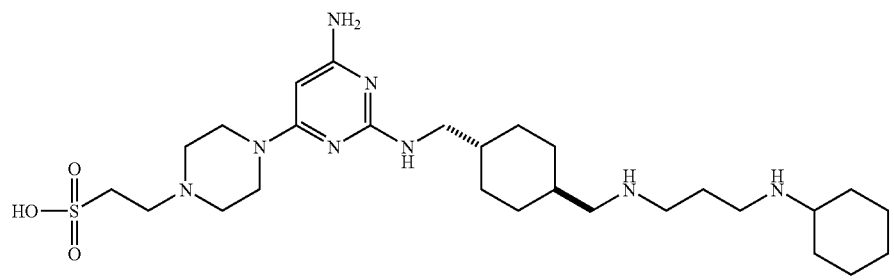

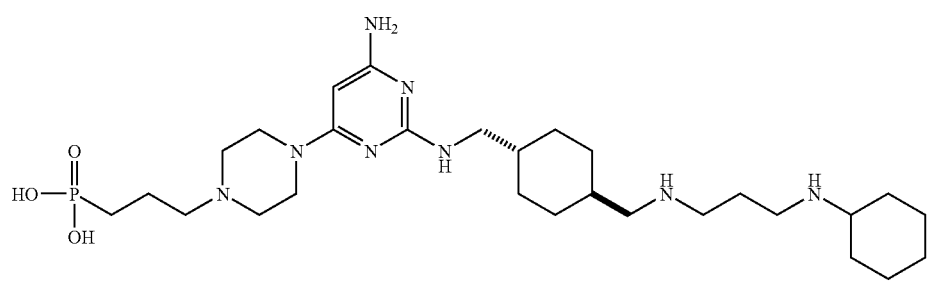

-continued
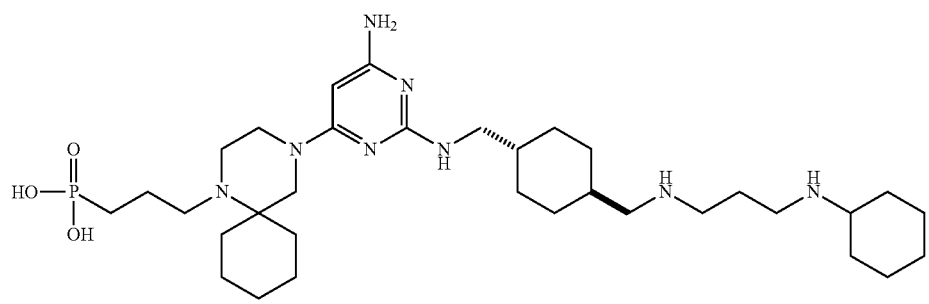
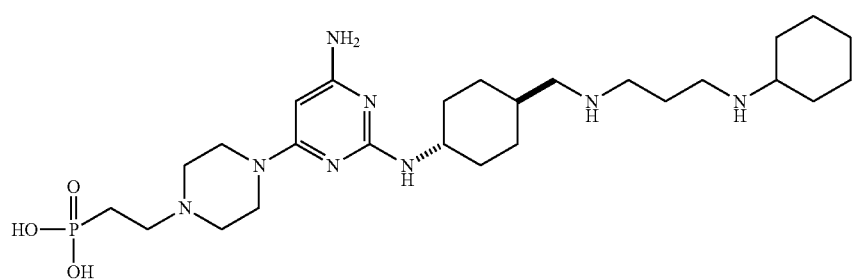
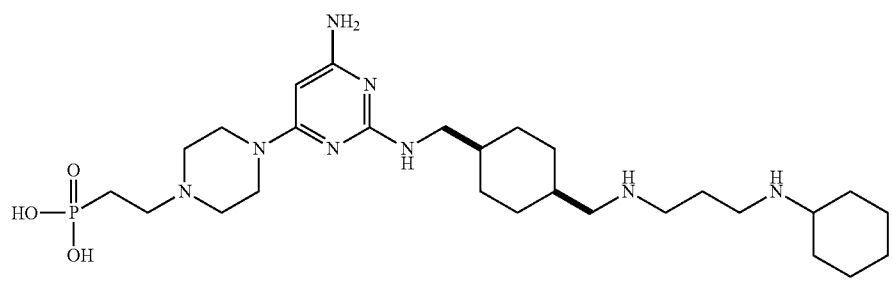
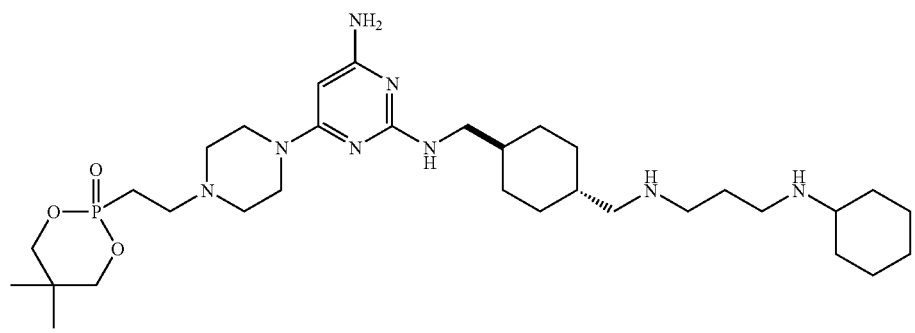
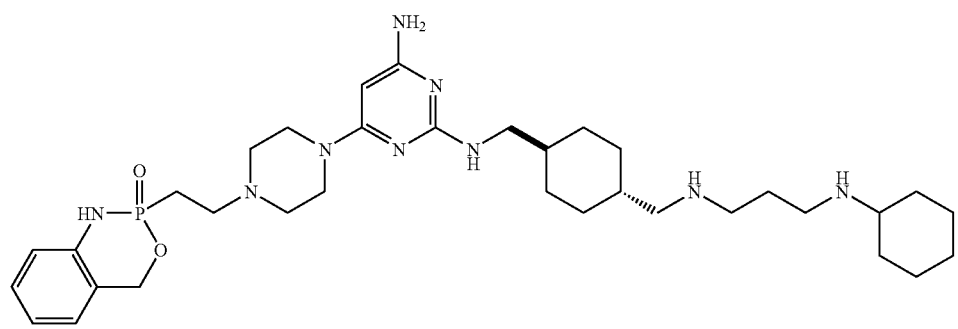

-continued

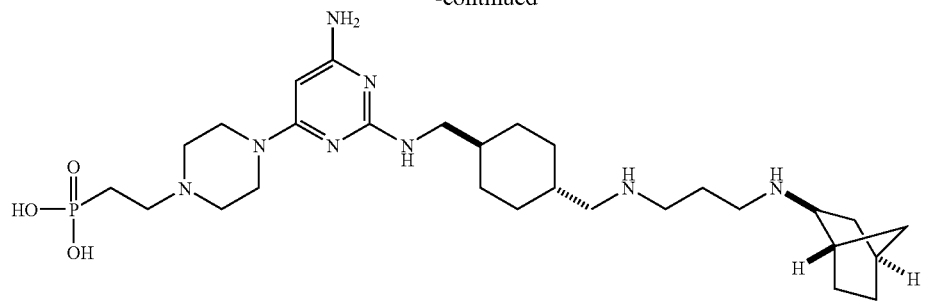

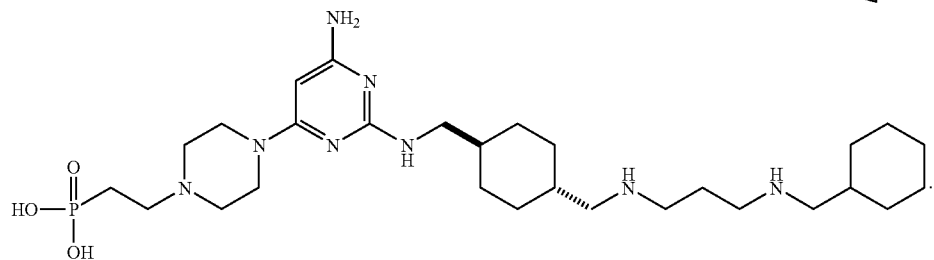

6. The pharmaceutical kit of claim 1, further comprising a bulking agent.

7. The pharmaceutical kit of claim 6, wherein the kit is free of a tonicity adjuster.

8. The pharmaceutical kit of claim 6, wherein the kit is free of sodium chloride.

9. The pharmaceutical kit of claim 6, wherein the bulking agent is mannitol or dextran.

10. The pharmaceutical kit of claim 9, wherein X is —$CH_2$—, —$CH_2CH_2$— or —$CH_2CH_2CH_2$—; Y is —$CH_2$— or deleted and Z is —$CH_2$—; $R_1$ is $NH_2$; $R_2$ is ($C_{1-5}$ alkyl)-NH—($C_{3-10}$ cycloalkyl).

11. The pharmaceutical kit of claim 1, wherein $R_3$ is P(=O)(OH)$_2$, P(=O)(OH)(OCH$_2$CH$_3$), P(=O)(OCH$_2$CH$_3$)$_2$, S(=O)$_2$OH, S(=O)$_2$CH$_3$, or S(=O)$_2$Ph.

12. The pharmaceutical kit of claim 11, wherein the lyophilized compound is one of the compounds shown below:

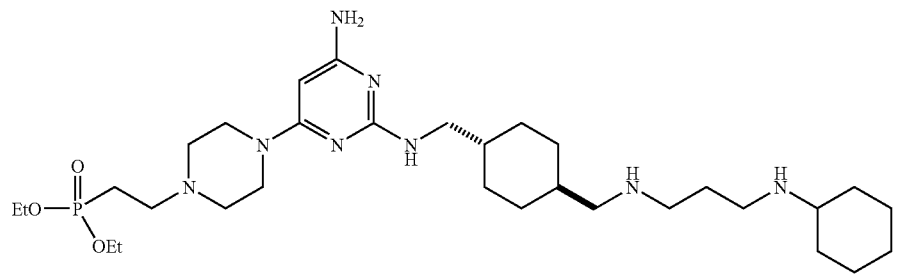

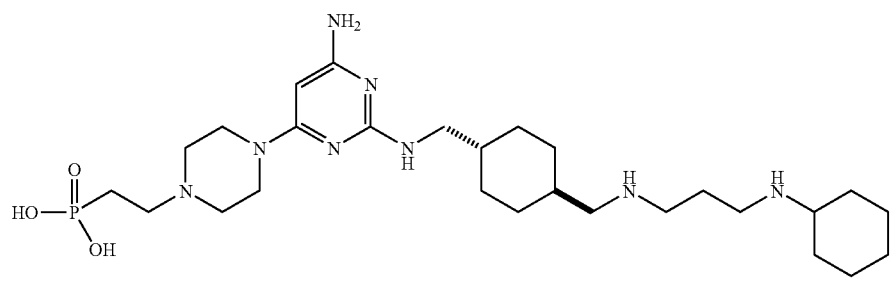

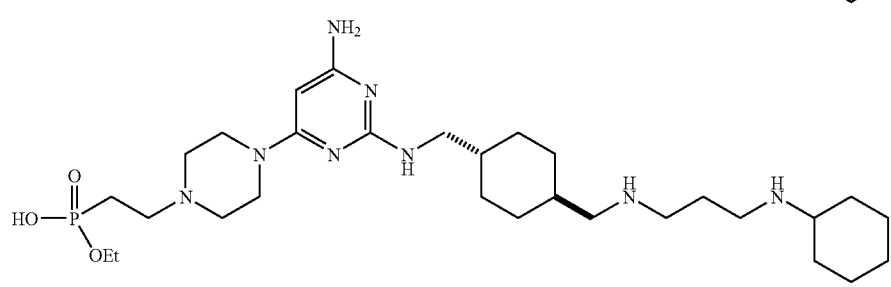

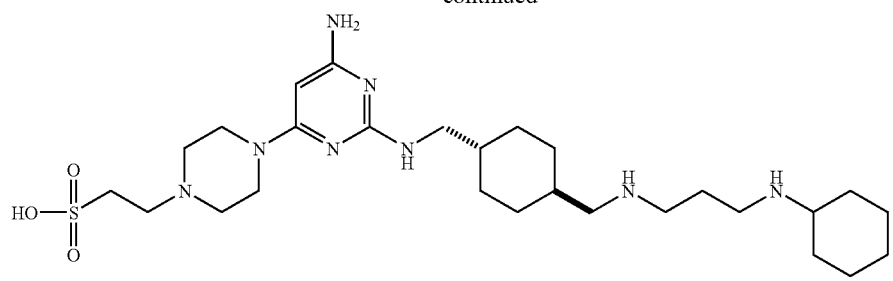
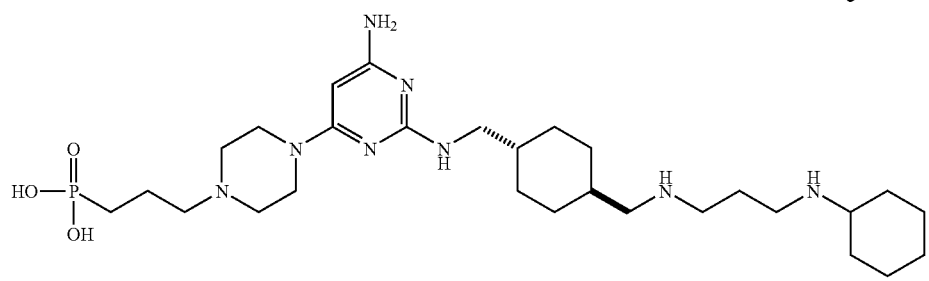
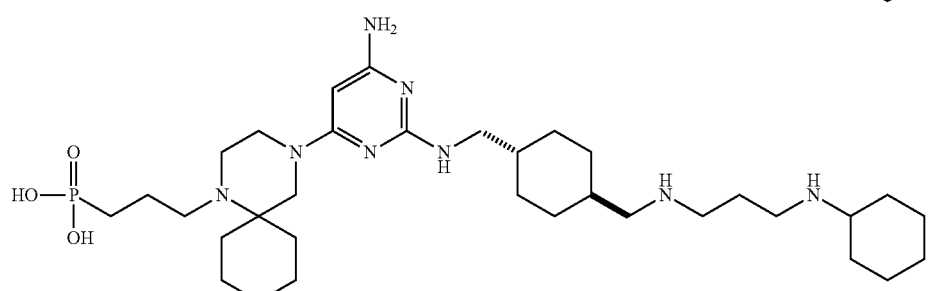
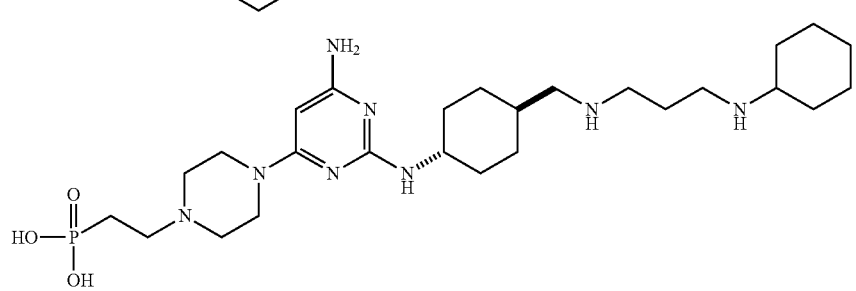
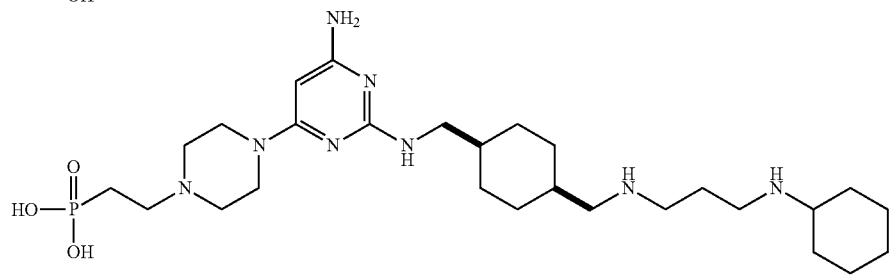
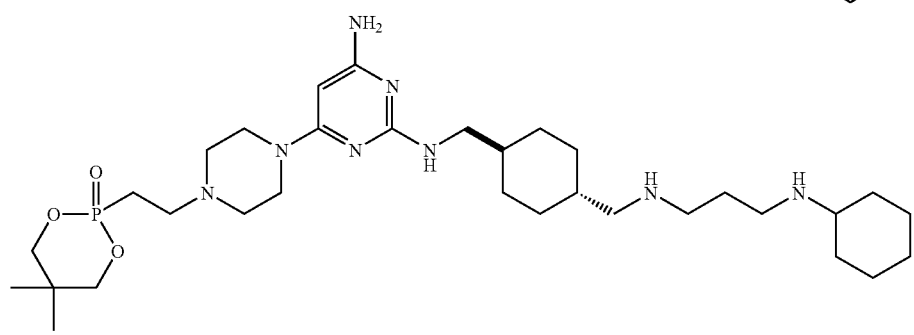

-continued

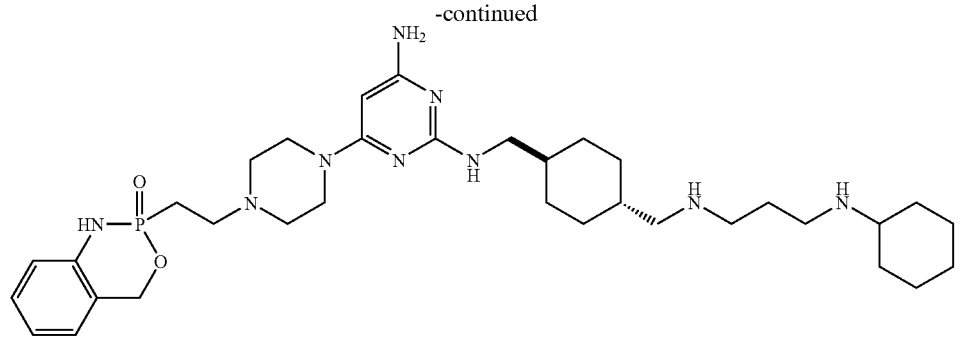

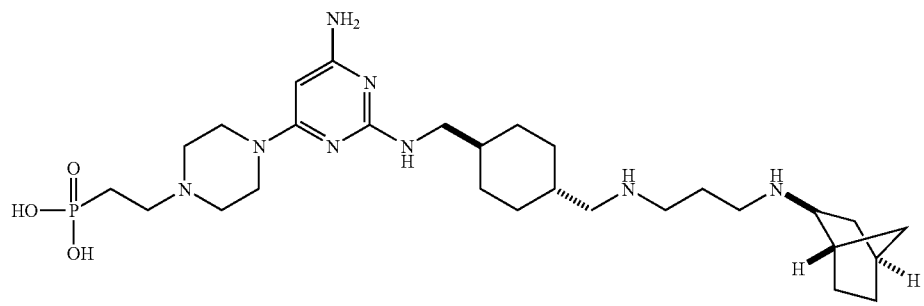

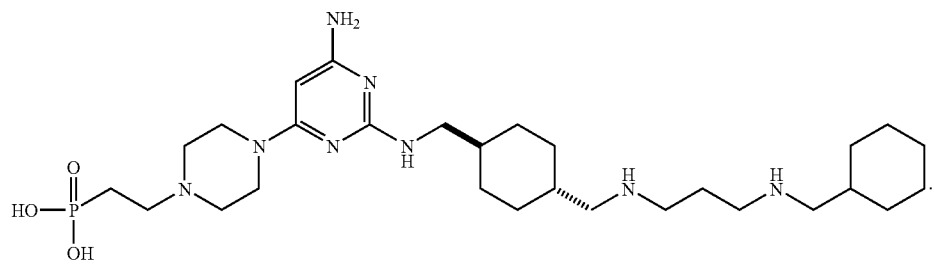

13. The pharmaceutical kit of claim 1, further comprising a tonicity adjuster.

14. The pharmaceutical kit of claim 13, wherein the tonicity adjuster is sodium chloride.

15. The pharmaceutical kit of claim 1, further comprising a bulking agent and a tonicity adjuster, wherein the weight ratio between the compound, the bulking agent, and the tonicity adjuster is 1-25:10-50:0.01-6.

16. The pharmaceutical kit of claim 1, further comprising a bulking agent and a tonicity adjuster, wherein the weight ratio between the compound, the bulking agent, and the tonicity adjuster is 1-50:0.01-50:0.01-0.9.

17. The pharmaceutical kit of claim 16, wherein the lyophilized compound is one of the compounds shown below:

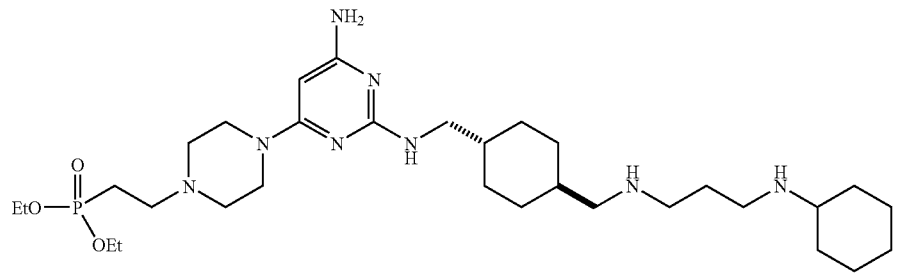

-continued
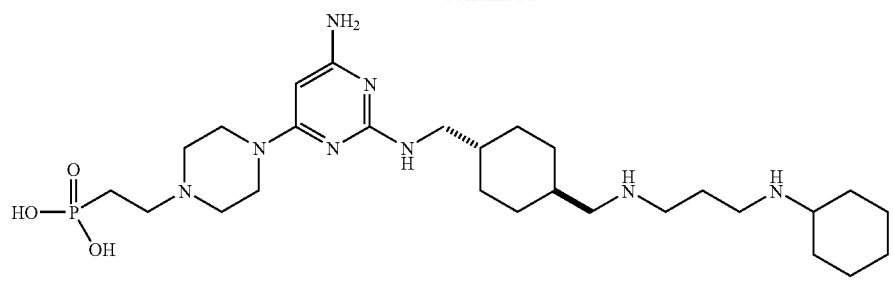
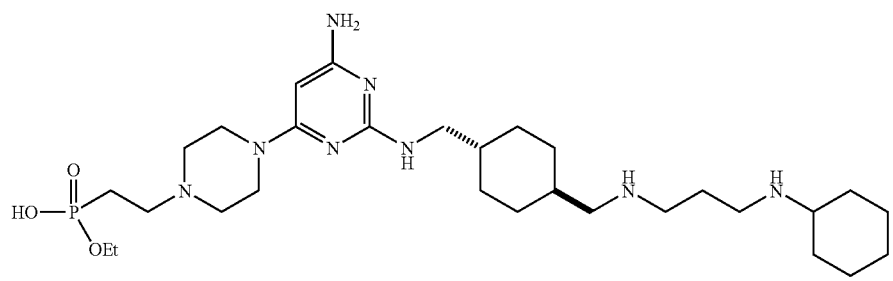
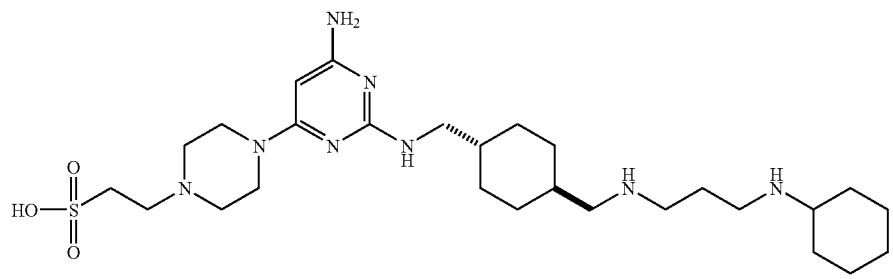
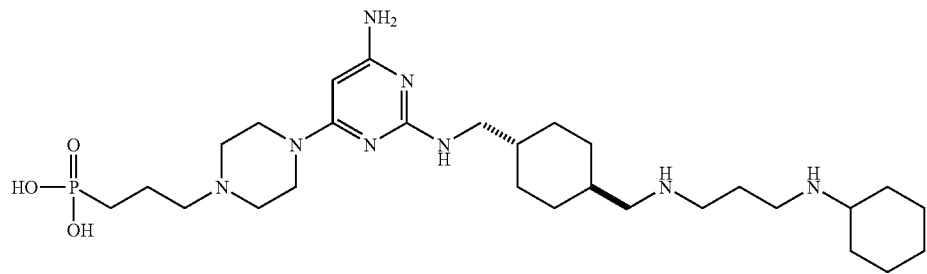
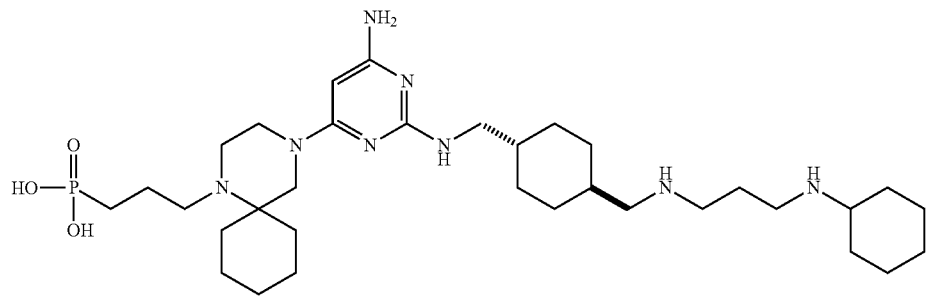
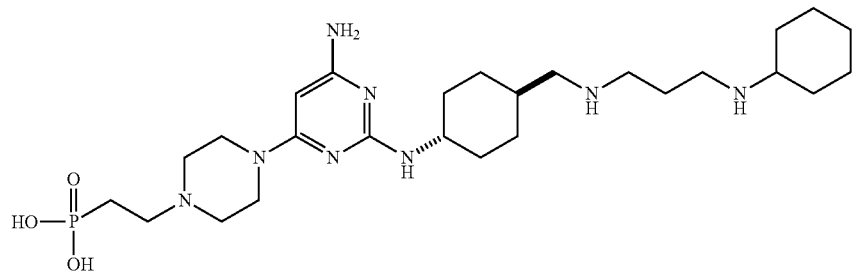

-continued
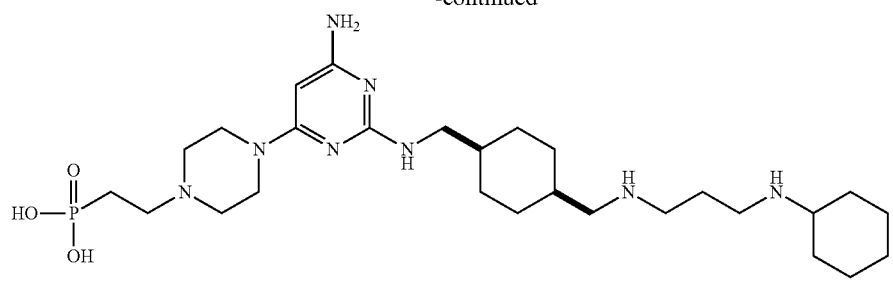
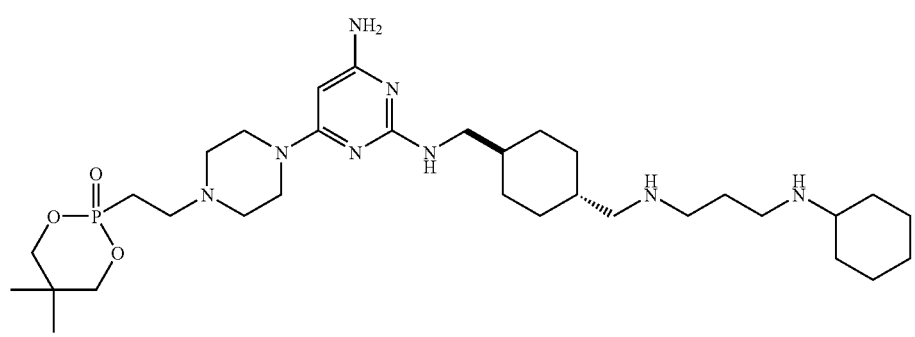
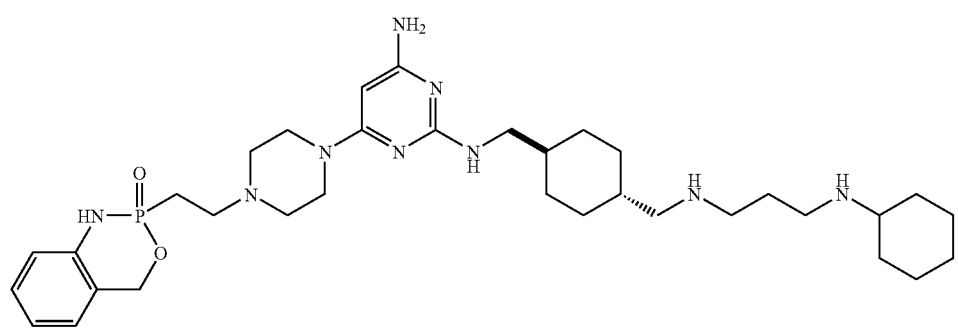
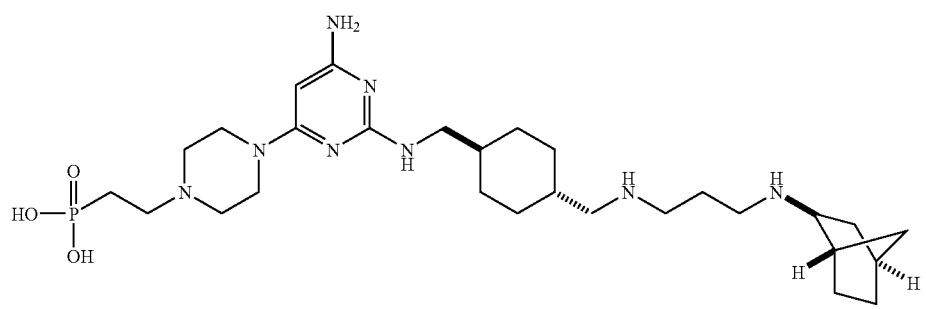
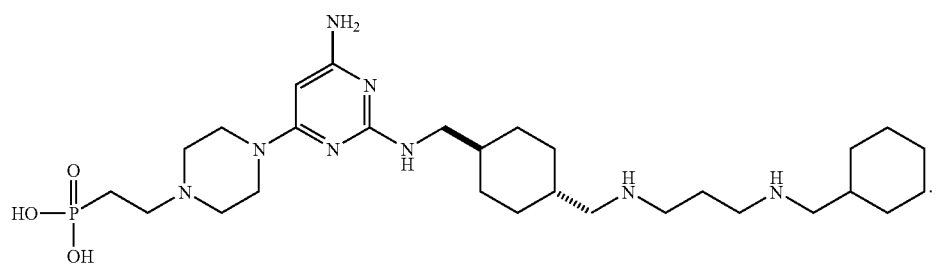

18. A process of making a lyophilized preparation of a compound having the following formula:

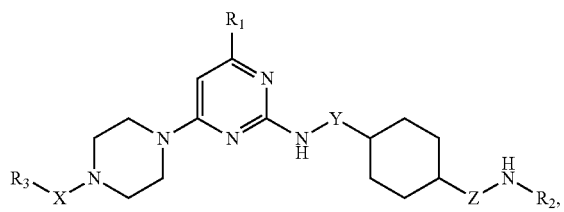

wherein
each of X, Y, and Z, independently, is $C_{1-5}$ alkylene or deleted;
$R_1$ is H, $C_{1-5}$ alkyl, OH, or $NH_2$;
$R_2$ is $C_{3-10}$ cycloalkyl or $(C_{1-5}$ alkyl$)$-NH—$(C_{3-10}$ cycloalkyl); and
$R_3$ is $P(=O)(OH)_2$, $P(=O)(OH)(OC_{1-5}$ alkyl$)$, $P(=O)(OC_{1-5}$ alkyl$)_2$, $S(=O)_2(OH)$, $S(=O)_2C_{1-5}$ alkyl, or $S(=O)_2Ph$; and
the process comprising:
providing an aqueous solution containing the compound;
cooling the solution to a temperature between −80° C. and −10° C.; and
vacuuming the cooled solution between −80° C. and −10° C. for 15-100 hours, and then between −9° C. and 35° C. for 10-200 hours.

19. The process of claim 18, wherein the aqueous solution further contains a bulking agent.

20. The process of claim 18, wherein the aqueous solution further contains a tonicity adjuster.

21. The process of claim 18, wherein the aqueous solution further contains bulking agent and a tonicity adjuster.

22. The process of claim 21, wherein the bulking agent is mannitol or dextran and the tonicity adjuster is sodium chloride.

23. The process of claim 22, wherein, before the cooling step, the aqueous solution contains 1-50 mg/ml of the compound based on its free base form, 0.01-50 mg/ml mannitol or dextran, and 0.01-6 mg/ml sodium chloride.

24. The process of claim 18, wherein, before the cooling step, the aqueous solution is sterilized by micro-filtration.

25. A lyophilized preparation made by a process comprising:
providing an aqueous solution containing a compound of the following formula:

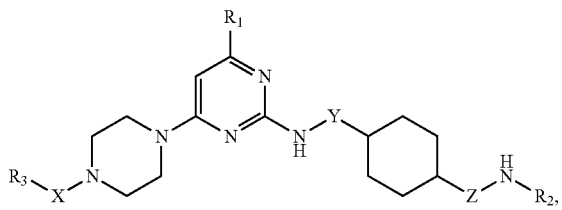

wherein
each of X, Y, and Z, independently, is $C_{1-5}$ alkylene or deleted;
$R_1$ is H, $C_{1-5}$ alkyl, OH, or $NH_2$;
$R_2$ is $C_{3-10}$ cycloalkyl or $(C_{1-5}$ alkyl$)$-NH—$(C_{3-10}$ cycloalkyl); and
$R_3$ is $P(=O)(OH)_2$, $P(=O)(OH)(OC_{1-5}$ alkyl$)$, $P(=O)(OC_{1-5}$ alkyl$)_2$, $S(=O)_2(OH)$, $S(=O)_2C_{1-5}$ alkyl, or $S(=O)_2Ph$;
cooling the solution to a temperature between −80° C. and −10° C.; and
vacuuming the cooled solution between −80° C. and −10° C. for 15-100 hours, and then between −9° C. and 35° C. for 10-200 hours.

26. The lyophilized preparation of claim 25, wherein, the process further comprises, before the cooling step, sterilizing the solution micro-filtration.

* * * * *